US007732402B2

(12) United States Patent
Villeponteau et al.

(10) Patent No.: US 7,732,402 B2
(45) Date of Patent: *Jun. 8, 2010

(54) MAMMALIAN TELOMERASE

(75) Inventors: Bryant Villeponteau, San Carlos, CA (US); Junli Feng, San Carlos, CA (US); Walter Funk, Union City, CA (US); William Andrews, Reno, NV (US)

(73) Assignee: Geron Corporation, Menlo Park, CA (US)

( * ) Notice: Subject to any disclaimer, the term of this patent is extended or adjusted under 35 U.S.C. 154(b) by 1718 days.

This patent is subject to a terminal disclaimer.

(21) Appl. No.: 10/359,935

(22) Filed: Feb. 7, 2003

(65) Prior Publication Data

US 2003/0153076 A1    Aug. 14, 2003

Related U.S. Application Data

(63) Continuation of application No. 09/057,351, filed on Apr. 8, 1998, now Pat. No. 6,548,298, which is a continuation of application No. 08/472,802, filed on Jun. 7, 1995, now Pat. No. 5,958,680, which is a continuation-in-part of application No. 08/330,123, filed on Oct. 27, 1994, now Pat. No. 5,583,016, which is a continuation-in-part of application No. 08/272,102, filed on Jul. 7, 1994, now abandoned.

(51) Int. Cl.
*A61K 31/70* (2006.01)
*C12Q 1/68* (2006.01)
(52) U.S. Cl. .............................. 514/4; 435/6
(58) Field of Classification Search .................. 514/44; 435/6
See application file for complete search history.

(56) References Cited

U.S. PATENT DOCUMENTS

| 4,737,454 | A |  | 4/1988 | Dattagupta et al. |
| 5,270,201 | A |  | 12/1993 | Richards et al. |
| 5,489,508 | A |  | 2/1996 | West et al. |
| 5,496,698 | A |  | 3/1996 | Draper et al. |
| 5,583,016 | A |  | 12/1996 | Villeponteau et al. |
| 5,643,890 | A |  | 7/1997 | Iversen et al. ............. 514/44 |
| 5,645,986 | A |  | 7/1997 | West et al. |
| 5,958,680 | A | * | 9/1999 | Villeponteau et al. ........ 435/6 |
| 6,548,298 | B2 | * | 4/2003 | Villeponteau et al. ....... 435/375 |

FOREIGN PATENT DOCUMENTS

| EP | 0 666 313 A2 | 8/1995 |
| JP | 10-234384 | 9/1998 |
| WO | 9002757 | 3/1990 |
| WO | WO-92/02228 | 2/1992 |
| WO | WO-93/23572 | 11/1993 |
| WO | WO-95/13382 | 5/1995 |
| WO | WO-96/01614 | 1/1996 |
| WO | WO-96/01835 | 1/1996 |
| WO | WO-98/07838 | 2/1998 |

OTHER PUBLICATIONS

Scherer et al. (Nat. Biotechnol., 2003, 21(12), pp. 1457-1465).*
Jen et al. (Stem Cells, 2000, vol. 18, p. 307-319).*
Opalinska et al. (Nature Reviews Drug Discovery, 2002, vol. 1, p. 503-514).*
Braasch et al. (Biochemistry 2002, vol. 41(14), pp. 4503-4510).*
Branch et al. (Trends Biochem Sci, 1998, vol. 23(2), pp. 45-50).*
Blackburn (1991), "Structure and function of telomeres," *Nature* 350:569-573.
Blackburn (1992), "Telomerases," *Ann. Rev. Biochem.* 61:113-129.
Blackburn et al. (Jan. 1989), "Recognition and elongation of telomeres by telomerase," *Genome* 31:553-560.
Counter et al. (1992), "Telomere shortening associated with chromosome instability is arrested in immortal cells which express telomerase activity," *EMBO J.* 11(5):1921-1929.
Czech (Nov. 25, 1988), "Ribozymes and their medical implications," *JAMA* 260 (20):3030-3034.
Eck and Nabel (1991), "Antisense oligonucleotides for therapeutic intervention," *Current Opinions Biotechnology* 2:897-904.
Greider (Sep. 1991), "Telomerase is processive," *Mol. Cell. Bio.* 11:4572-4580.
Greider and Blackburn (Dec. 24, 1987), "The telomere terminal transferase of Tetrahymena is a ribonucleoprotein enzyme with two kinds of primer specificity," *Cell* 51:887-898.
Greider and Blackburn (Jan. 26, 1989), "A telomeric sequence in the RNA of Tetrahymena telomerase required for telomere repeat synthesis," *Nature* 337 (6205):331-337.
Harley et al. (May 31, 1990), "Telomeres shorten during ageing of human fibroblasts," *Nature* 345:458-460.
Harley et al. (1991), "Telomere loss: Mitotic clock or genetic time bomb?" *Mut. Res.* 256:271-282.
Morin (Nov. 3, 1989), "The human telomere terminal transferase enzyme is a ribonucleoprotein that synthesizes TTAGGG Repeats," *Cell*, 59:521-529.
Morin (Oct. 8, 1991), "Recognition of a chromosome truncation site associated with alpha-thalassaemia by human telomerase," *Nature* 353:454-456.
Romero and Blackburn (Oct. 18, 1991), "A conserved secondary structure for telomerase RNA," *Cell* 67:343-353.
Shippen-Lentz and Blackburn (Feb. 2, 1990), "Functional evidence for an RNA template in telomerase," *Science* 247:546-552.
Yu et al. (Mar. 8, 1990), "In vitro alteration of telomere sequences and senescence caused by mutated Tetrahymena telomerase RNAs," *Nature* 344:126-132.
Yu and Blackburn (Nov. 15, 1991), "Developmentally programmed healing of chromosomes by telomerase in Tetrahymena," *Cell* 67:823-832.
Zahler et al. (Apr. 25, 1991), "Inhibition of telomerase by G-quartet DNA structures," *Nature* 350:718-720.
Lingner et al. (1984), "Telomerase RNAs of different ciliates have a common secondary structure and a permuted template," *Genes and Development* 8:1989-1998.
Singer and Gottschling (1994), "TLC1: Template RNA Component of *Saccharomyces cerevisiae* Telomerase," *Science* 266:404-409.

(Continued)

*Primary Examiner*—J. E Angell
(74) *Attorney, Agent, or Firm*—David J. Earp; Leslie A. Mooi

(57) ABSTRACT

Nucleic acids comprising the RNA component of a mammalian telomerase are useful as pharmaceutical, therapeutic, and diagnostic reagents.

7 Claims, 6 Drawing Sheets

OTHER PUBLICATIONS

Kim et al. (1994), "Specific Association of Human Telomerase Activity with Immortal Cells and Cancer," *Science* 266:2011-2014.
Blackburn, E.H., "Telomeres," *TIBS*, 16:378-381 (1991).
Blackburn, E.H., Grant Abstracts 5R01 GM 32565-11; 5P30 ES01896-15UB; 5R37 GM26259-16.
Counter et al., "Telomerase activity in human overian carcinoma," *PNAS*, 91:2900-2904 (1994).
Feng, J. et al., "The RNA Component of Human Telomerase," *Science*, 269 1236-1241 (1995).
Grieder, C.W., "Telomerase and Telomere-length Regulation: Lessons from Small Eukaryotes to Mammals," *Cold Spring Harbor Symposia on Quantitative Biology*, vol. LVIII, Cold Spring Harbor Laboratory, New York (1993).
Grieder, C.W., Grant Abstracts 5R01 RG09383-03; 5R01 GM43080-04.
Nilsson, P. et al., "Telomerase activity in vivo in human malignant hematopoietic cells," *Oncogene*, 9:3043-3048 (1994).
Prowse, et al., "Identification of a nonprocessive telomerase activity from mouse cells," *Proc. Nat. Acad. Sci. USA*, 90:1493-1497 (1993).
Rennie, J., "Immortal's Enzyme," *Scientific American*, Jul. 1994, pp. 14-16 (1994).
Rensberger, B. "Cancer's Immortality May Depend on Enzyme," *Washington Post*, Apr. 12, 1994, p. A1, A12.
Yan et al., "Amino Acid Sequence of the Human Protein Synthesis Initiation Factor eIF-4γ," *J. Biol. Chem.*, 267:23226-23231 (1992).
Pestka et al., "Antisense RNA, History and perspective." *Ann. N.Y. Acad. Sci.* vol. 660:251-262.
Xiao et al., "Adeno-associated virus (AAV) vectors for gene transfer," *Adv. Drug Del. Rev.* vol. 12:201-215.
Chatterjee et al., "Dual-target inhibition of HIV-1 in vitro by means of an adeno-associated virus antisense vector," *Science*, vol. 258:1485-1488.
Dahse et al., "Telomeres and telomerase: biological and clinical importance," *Clin. Chem.* vol. 43(5):708-714.

Marshall, "Gene therapy's growing pains," *Science* vol. 269:1050-1055.
Alam, J. et al., "Reporter genes: application to the study of mammalian gene transcription," *Anal. Biochem* 188(2) (1990), pp. 245-254.
Autexier, C. et al., "Functional reconstitution of wild-type and mutant Tetrahymena telomerase," *Genes Dev.* 8 (1994), pp. 563-575.
Blasco, M. et al., "Functional characterization and developmental regulatoin of mouse telomerase RNA," *Science 269* (1995), pp. 1267-1270.
Flanagan, W. et al., "Cellular penetration and antisense activity by a phenoxazine-substituted heptanucleotide," *Nature Biotechnol. 17*(1) (1999), pp. 48-52.
Greider, C. et al., "Telomeres, telomerase and cancer," *Sci. Am. 274*(2) (1996), pp. 92-97.
Harley, C. et al., "Human telomerase inhibition and cancer," *Proc. of the Annual Meeting of the Amer. Assoc. for Cancer Res.*, Toronto, Canada, Mar. 18-22, 1995 Abstract (1995), pp. 671-672.
Harley, C., "Telomeres and Aging: Fact, Fancy, and the Future," *J. NIH Res.* 7 (1995), pp. 64-68.
Harley, C. et al., "Telomeres and telomerase in aging and cancer," *Curr. Op. Genet. Dev. 5* (1995), pp. 249-255.
Li, X. et al., "The water channel gene in human uterus," *Biochem. Mol. Biol. Int. 32*(2) (1994), pp. 371-377.
Mehle, C. et al., "Telomere shortening in renal cell carcinoma," *Cancer Res. 54*(1) (1994), pp. 236-241.
Paau, A., *Iowa State University Letter re Novel Gene Therapy for Cancers Abstract* (Feb. 24, 1995), 2 pages.
Palmiter, R. et al., "Cell lineage ablation in transgenic mice by cell-specific expression of a toxin gene," *Cell 50*(3) (1987), pp. 435-443.
Villeponteau, B. et al., "The RNA components of human and mouse telomerases," *Sem. Cell Dev. Biol.* 7 (1996), pp. 15-21.
Wahlfors, J., "EMBL Database entry," *HSSATALU, 44 Sequence database entry* (Mar. 17, 1993), 3 pages.
Zhao, J. et al., "Cloning and characterization of human and mouse telomerase RNA gene promoter sequences," *Oncogene 16*(10) (1998), pp. 1345-1350.

* cited by examiner

SEQUENCE LISTING (1) GENERAL INFORMATION:

(iii) NUMBER OF SEQUENCES: 42

(2) INFORMATION FOR SEQ ID NO: 1:

(i) SEQUENCE CHARACTERISTICS:
      (A) LENGTH: 560 base pairs
      (B) TYPE: nucleic acid
      (C) STRANDEDNESS: single
      (D) TOPOLOGY: linear (ii) MOLECULE TYPE: RNA (genomic)

(xi) SEQUENCE DESCRIPTION: SEQ ID NO: 1:

GGGUUGCGGA GGGUGGGCCU GGGAGGGGUG GUGGCCAUUU UUUGUCUAAC CCUAACUGAG   60

| | |
|---|---:|
| AAGGGCGUAG GCGCCGUGCU UUUGCUCCCC GCGCGCUGUU UUUCUCGCUG ACUUUCAGCG | 120 |
| GGCGGAAAAG CCUCGGCCUG CCGCCUUCCA CCGUUCAUUC UAGAGCAAAC AAAAAAUGUC | 180 |
| AGCUGCUGGC CCGUUCGCCC CUCCCGGGGA CCUGCGGCGG GUCGCCUGCC CAGCCCCCGA | 240 |
| ACCCCGCCUG GAGGCCGCGG UCGGCCCGGG GCUUCUCCGG AGGCACCCAC UGCCACCGCG | 300 |
| AAGAGUUGGG CUCUGUCAGC CGCGGGUCUC UCGGGGGCGA GGGCGAGGUU CAGGCCUUUC | 360 |
| AGGCCGCAGG AAGAGGAACG GAGCGAGUCC CCGCGCGCGG CGCGAUUCCC UGAGCUGUGG | 420 |
| GACGUGCACC CAGGACUCGG CUCACACAUG CAGUUCGCUU UCCUGUUGGU GGGGGGAACG | 480 |
| CCGAUCGUGC GCAUCCGUCA CCCCUCGCCG GCAGUGGGGG CUUGUGAACC CCCAAACCUG | 540 |
| ACUGACUGGG CCAGUGUGCU | 560 |

(2) INFORMATION FOR SEQ ID NO: 2:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 2:

| | |
|---|---:|
| CUAACCCUAA C | 11 |

(2) INFORMATION FOR SEQ ID NO: 3:

(i) SEQUENCE CHARACTERISTICS:
        (A) LENGTH: 2426 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

| | |
|---|---:|
| GATCAGTTAG AAAGTTACTA GTCCACATAT AAAGTGCCAA GTCTTGTACT CAAGATTATA | 60 |
| AGCAATAGGA ATTTAAAAAA AGAAATTATG AAAACTGACA AGATTTAGTG CCTACTTAGA | 120 |
| TATGAAGGGG AAAGAAGGGT TTGAGATAAT GTGGGATGCT AAGAGAATGG TGGTAGTGTT | 180 |
| GACATATAAC TCAAAGCATT TAGCATCTAC TCTATGTAAG GTACTGTGCT AAGTGCAATA | 240 |
| GTGCTAAAAA CAGGAGTCAG ATTCTGTCCG TAAAAAACTT TACAACCTGG CAGATGCTAT | 300 |
| GAAAGAAAAA GGGGATGGGA GAGAGAGAAG GAGGGAGAGA GATGGAGAGG GAGATATTTT | 360 |
| ACTTTTCTTT CAGATCGAGG ACCGACAGCG ACAACTCCAC GGAGTTTATC TAACTGAATA | 420 |
| CGAGTAAAAC TTTTAAGATC ATCCTGTCAT TTATATGTAA AACTGCACTA TACTGGCCAT | 480 |
| TATAAAAATT CGCGGCCGGG TGCGGTGGCT CATACCTGTA ATCCCAGCAC TTTGGGAGGC | 540 |
| CGAAGCGGGT GGATCACTTG AGCCCTGGCG TTCGAGACCA GCCTGGGCAA CATGGTGAAA | 600 |
| CCCCCGTCTC TACTAAAAAC ACAAAAACTA GCTGGGCGTG GTGGCAGGCG CCTGTAATCC | 660 |
| CAGCTACTCA GGAGGCTGAG ACACGAGAAT CGCTTGAACC CGGGAGCAGA GGTTGCAGTG | 720 |
| AGCCGAGATC ACGCCACTAG ACTCCATCCA GCCTGGGCGA AAGAGCAAGA CTCCGTCTCA | 780 |
| AAAAAAAAAA TCGTTACAAT TTATGGTGGA TTACTCCCCT CTTTTTACCT CATCAAGACA | 840 |
| CAGCACTACT TTAAAGCAAA GTCAATGATT GAAACGCCTT TCTTTCCTAA TAAAAGGGAG | 900 |
| ATTCAGTCCT TAAGATTAAT AATGTAGTAG TTACACTTGA TTAAAGCCAT CCTCTGCTCA | 960 |
| AGGAGAGGCT GGAGAAGGCA TTCTAAGGAG AAGGGGGCAG GGTAGGAACT CGGACGCATC | 1020 |

```
CCACTGAGCC GAGACAAGAT TCTGCTGTAG TCAGTGCTGC CTGGGAATCT ATTTTCACAA      1080

AGTTCTCCAA AAAATGTGAT GATCAAAACT AGGAATTAGT GTTCTGTGTC TTAGGCCCTA      1140

AAATCTTCCT GTGAATTCCA TTTTTAAGGT AGTCGAGGTG AACCGCGTCT GGTCTGCAGA      1200

GGATAGAAAA AAGGCCCTCT GATACCTCAA GTTAGTTTCA CCTTTAAAGA AGGTCGGAAG      1260

TAAAGACGCA AAGCCTTTCC CGGACGTGCG AAGGGCAAC GTCCTTCCTC ATGGCCGGAA       1320

ATGGAACTTT AATTTCCCGT TCCCCCCAAC CAGCCCGCCC GAGAGAGTGA CTCTCACGAG      1380

AGCCGCGAGA GTCAGCTTGG CCAATCCGTG CGGTCGGCGG CCGCTCCCTT TATAAGCCGA      1440

CTCGCCCGGC AGCGCACCGG GTTGCGGAGG GTGGGCCTGG GAGGGGTGGT GGCCATTTTT      1500

TGTCTAACCC TAACTGAGAA GGGCGTAGGC GCCGTGCTTT TGCTCCCCGC GCGCTGTTTT      1560

TCTCGCTGAC TTTCAGCGGG CGGAAAAGCC TCGGCCTGCC GCCTTCCACC GTTCATTCTA      1620

GAGCAAACAA AAAATGTCAG CTGCTGGCCC GTTCGCCCCT CCCGGGGACC TGCGGCGGGT      1680

CGCCTGCCCA GCCCCGAAC CCCGCCTGGA GGCCGCGGTC GGCCCGGGGC TTCTCCGGAG       1740

GCACCCACTG CCACCGCGAA GAGTTGGGCT CTGTCAGCCG CGGGTCTCTC GGGGGCGAGG      1800

GCGAGGTTCA GGCCTTTCAG GCCGCAGGAA GAGGAACGGA GCGAGTCCCC GCGCGCGGCG      1860

CGATTCCCTG AGCTGTGGGA CGTGCACCCA GGACTCGGCT CACACATGCA GTTCGCTTTC      1920

CTGTTGGTGG GGGGAACGCC GATCGTGCGC ATCCGTCACC CCTCGCCGGC AGTGGGGGCT      1980

TGTGAACCCC CAAACCTGAC TGACTGGGCC AGTGTGCTGC AAATTGGCAG GAGACGTGAA      2040

GGCACCTCCA AAGTCGGCCA AAATGAATGG GCAGTGAGCC GGGGTTGCCT GGAGCCGTTC      2100

CTGCGTGGGT TCTCCCGTCT TCCGCTTTTT GTTGCCTTTT ATGGTTGTAT TACAACTTAG      2160

TTCCTGCTCT GCAGATTTTG TTGAGGTTTT TGCTTCTCCC AAGGTAGATC TCGACCAGTC      2220

CCTCAACGGG GTGTGGGGAG AACAGTCATT TTTTTTTGAG AGATCATTTA ACATTTAATG      2280

AATATTTAAT TAGAAGATCT AAATGAACAT TGGAAATTGT GTTCCTTTAA TGGTCATCGG      2340

TTTATGCCAG AGGTTAGAAG TTTCTTTTTT GAAAAATTAG ACCTTGGCGA TGACCTTGAG      2400

CAGTAGGATA TAACCCCCAC AAGCTT                                          2426
```

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: RNA (ix) FEATURE:
        (A) NAME/KEY: modified_base
        (B) LOCATION: 1
        (D) OTHER INFORMATION: /mod_base= cm (ix) FEATURE:
        (A) NAME/KEY: modified_base
        (B) LOCATION: 2
        (D) OTHER INFORMATION: /mod_base= um (ix) FEATURE:
        (A) NAME/KEY: modified_base
        (B) LOCATION: 3
        (D) OTHER INFORMATION: /mod_base= cm (ix) FEATURE:
        (A) NAME/KEY: modified_base
        (B) LOCATION: 4
        (D) OTHER INFORMATION: /mod_base= OTHER -continued

```
              /note= "N = 2'-O-methyl-riboadenine"

(ix) FEATURE:
         (A) NAME/KEY: modified_base
         (B) LOCATION: 5
         (D) OTHER INFORMATION: /mod_base= gm (ix) FEATURE:
         (A) NAME/KEY: modified_base
         (B) LOCATION: 6
         (D) OTHER INFORMATION: /mod_base= um (ix) FEATURE:
         (A) NAME/KEY: modified_base
         (B) LOCATION: 7
         (D) OTHER INFORMATION: /mod_base= um (ix) FEATURE:
         (A) NAME/KEY: modified_base
         (B) LOCATION: 8
         (D) OTHER INFORMATION: /mod_base= OTHER
              /note= "N = 2'-O-methyl-riboadenine"

(ix) FEATURE:
         (A) NAME/KEY: modified_base
         (B) LOCATION: 9
         (D) OTHER INFORMATION: /mod_base= gm (ix) FEATURE:
         (A) NAME/KEY: modified_base
         (B) LOCATION: 10
         (D) OTHER INFORMATION: /mod_base= gm (ix) FEATURE:
         (A) NAME/KEY: modified_base
         (B) LOCATION: 11
         (D) OTHER INFORMATION: /mod_base= gm (ix) FEATURE:
         (A) NAME/KEY: modified_base
         (B) LOCATION: 12
         (D) OTHER INFORMATION: /mod_base= um (ix) FEATURE:
         (A) NAME/KEY: modified_base
         (B) LOCATION: 13
         (D) OTHER INFORMATION: /mod_base= um (ix) FEATURE:
         (A) NAME/KEY: modified_base
         (B) LOCATION: 14
         (D) OTHER INFORMATION: /mod_base= OTHER
              /note= "N = 2'-O-methyl-riboadenine"

(ix) FEATURE:
         (A) NAME/KEY: modified_base
         (B) LOCATION: 15
         (D) OTHER INFORMATION: /mod_base= gm (ix) FEATURE:
         (A) NAME/KEY: modified_base
         (B) LOCATION: 16
         (D) OTHER INFORMATION: /mod_base= OTHER
              /note= "N = 2'-O-methyl-riboadenine"

(ix) FEATURE:
         (A) NAME/KEY: modified_base
         (B) LOCATION: 17
         (D) OTHER INFORMATION: /mod_base= cm (ix) FEATURE:
         (A) NAME/KEY: modified_base
         (B) LOCATION: 18
         (D) OTHER INFORMATION: /mod_base= OTHER
              /note= "N = 2'-O-methyl-riboadenine"

(ix) FEATURE:
         (A) NAME/KEY: modified_base
         (B) LOCATION: 19
```

(D) OTHER INFORMATION: /mod_base= OTHER
            /note= "N = 2'-O-methyl-riboadenine"

(ix) FEATURE:
        (A) NAME/KEY: modified_base
        (B) LOCATION: 20
        (D) OTHER INFORMATION: /mod_base= OTHER
            /note= "N = 2'-O-methyl-riboadenine"

(xi) SEQUENCE DESCRIPTION: SEQ ID NO: 4:

NNNNNNNNNN NNNNNNNNNN                                           20

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: RNA (ix) FEATURE:
        (A) NAME/KEY: modified_base
        (B) LOCATION: 1
        (D) OTHER INFORMATION: /mod_base= cm (ix) FEATURE:
        (A) NAME/KEY: modified_base
        (B) LOCATION: 2
        (D) OTHER INFORMATION: /mod_base= gm (ix) FEATURE:
        (A) NAME/KEY: modified_base
        (B) LOCATION: 3
        (D) OTHER INFORMATION: /mod_base= cm (ix) FEATURE:
        (A) NAME/KEY: modified_base
        (B) LOCATION: 4
        (D) OTHER INFORMATION: /mod_base= cm (ix) FEATURE:
        (A) NAME/KEY: modified_base
        (B) LOCATION: 5
        (D) OTHER INFORMATION: /mod_base= cm (ix) FEATURE:
        (A) NAME/KEY: modified_base
        (B) LOCATION: 6
        (D) OTHER INFORMATION: /mod_base= um (ix) FEATURE:
        (A) NAME/KEY: modified_base
        (B) LOCATION: 7
        (D) OTHER INFORMATION: /mod_base= um (ix) FEATURE:
        (A) NAME/KEY: modified_base
        (B) LOCATION: 8
        (D) OTHER INFORMATION: /mod_base= cm (ix) FEATURE:
        (A) NAME/KEY: modified_base
        (B) LOCATION: 9
        (D) OTHER INFORMATION: /mod_base= um (ix) FEATURE:
        (A) NAME/KEY: modified_base
        (B) LOCATION: 10
        (D) OTHER INFORMATION: /mod_base= cm (ix) FEATURE:
        (A) NAME/KEY: modified_base
        (B) LOCATION: 11
        (D) OTHER INFORMATION: /mod_base= OTHER
            /note= "N = 2'-O-methyl-riboadenine"

```
    (ix) FEATURE:
          (A) NAME/KEY: modified_base
          (B) LOCATION: 12
          (D) OTHER INFORMATION: /mod_base= gm (ix) FEATURE:
          (A) NAME/KEY: modified_base
          (B) LOCATION: 13
          (D) OTHER INFORMATION: /mod_base= um (ix) FEATURE:
          (A) NAME/KEY: modified_base
          (B) LOCATION: 14
          (D) OTHER INFORMATION: /mod_base= um (ix) FEATURE:
          (A) NAME/KEY: modified_base
          (B) LOCATION: 15
          (D) OTHER INFORMATION: /mod_base= OTHER
              /note= "N = 2'-O-methyl-riboadenine"

(ix) FEATURE:
          (A) NAME/KEY: modified_base
          (B) LOCATION: 16
          (D) OTHER INFORMATION: /mod_base= gm (ix) FEATURE:
          (A) NAME/KEY: modified_base
          (B) LOCATION: 17
          (D) OTHER INFORMATION: /mod_base= gm (ix) FEATURE:
          (A) NAME/KEY: modified_base
          (B) LOCATION: 18
          (D) OTHER INFORMATION: /mod_base= gm (ix) FEATURE:
          (A) NAME/KEY: modified_base
          (B) LOCATION: 19
          (D) OTHER INFORMATION: /mod_base= um (ix) FEATURE:
          (A) NAME/KEY: modified_base
          (B) LOCATION: 20
          (D) OTHER INFORMATION: /mod_base= um (ix) FEATURE:
          (A) NAME/KEY: modified_base
          (B) LOCATION: 21
          (D) OTHER INFORMATION: /mod_base= OTHER
              /note= "N = 2'-O-methyl-riboadenine"

(ix) FEATURE:
          (A) NAME/KEY: modified_base
          (B) LOCATION: 22
          (D) OTHER INFORMATION: /mod_base= gm (xi) SEQUENCE DESCRIPTION: SEQ ID NO: 5:

NNNNNNNNNN NNNNNNNNNN NN                                              22

(2) INFORMATION FOR SEQ ID NO: 6:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: RNA (ix) FEATURE:
          (A) NAME/KEY: modified_base
          (B) LOCATION: 1
          (D) OTHER INFORMATION: /mod_base= gm (ix) FEATURE:
```

```
            (A) NAME/KEY: modified_base
            (B) LOCATION: 2
            (D) OTHER INFORMATION: /mod_base= gm (ix) FEATURE:
            (A) NAME/KEY: modified_base
            (B) LOCATION: 3
            (D) OTHER INFORMATION: /mod_base= cm (ix) FEATURE:
            (A) NAME/KEY: modified_base
            (B) LOCATION: 4
            (D) OTHER INFORMATION: /mod_base= gm (ix) FEATURE:
            (A) NAME/KEY: modified_base
            (B) LOCATION: 5
            (D) OTHER INFORMATION: /mod_base= cm (ix) FEATURE:
            (A) NAME/KEY: modified_base
            (B) LOCATION: 6
            (D) OTHER INFORMATION: /mod_base= cm (ix) FEATURE:
            (A) NAME/KEY: modified_base
            (B) LOCATION: 7
            (D) OTHER INFORMATION: /mod_base= um (ix) FEATURE:
            (A) NAME/KEY: modified_base
            (B) LOCATION: 8
            (D) OTHER INFORMATION: /mod_base= OTHER
                /note= "N = 2'-O-methyl-riboadenine"

(ix) FEATURE:
            (A) NAME/KEY: modified_base
            (B) LOCATION: 9
            (D) OTHER INFORMATION: /mod_base= cm (ix) FEATURE:
            (A) NAME/KEY: modified_base
            (B) LOCATION: 10
            (D) OTHER INFORMATION: /mod_base= gm (ix) FEATURE:
            (A) NAME/KEY: modified_base
            (B) LOCATION: 11
            (D) OTHER INFORMATION: /mod_base= cm (ix) FEATURE:
            (A) NAME/KEY: modified_base
            (B) LOCATION: 12
            (D) OTHER INFORMATION: /mod_base= cm (ix) FEATURE:
            (A) NAME/KEY: modified_base
            (B) LOCATION: 13
            (D) OTHER INFORMATION: /mod_base= cm (ix) FEATURE:
            (A) NAME/KEY: modified_base
            (B) LOCATION: 14
            (D) OTHER INFORMATION: /mod_base= um (ix) FEATURE:
            (A) NAME/KEY: modified_base
            (B) LOCATION: 15
            (D) OTHER INFORMATION: /mod_base= um (ix) FEATURE:
            (A) NAME/KEY: modified_base
            (B) LOCATION: 16
            (D) OTHER INFORMATION: /mod_base= cm (ix) FEATURE:
            (A) NAME/KEY: modified_base
            (B) LOCATION: 17
            (D) OTHER INFORMATION: /mod_base= um
```

```
    (ix) FEATURE:
          (A) NAME/KEY: modified_base
          (B) LOCATION: 18
          (D) OTHER INFORMATION: /mod_base= cm (ix) FEATURE:
          (A) NAME/KEY: modified_base
          (B) LOCATION: 19
          (D) OTHER INFORMATION: /mod_base= OTHER
              /note= "N = 2'-O-methyl-riboadenine"

(ix) FEATURE:
          (A) NAME/KEY: modified_base
          (B) LOCATION: 20
          (D) OTHER INFORMATION: /mod_base= gm (ix) FEATURE:
          (A) NAME/KEY: modified_base
          (B) LOCATION: 21
          (D) OTHER INFORMATION: /mod_base= um (ix) FEATURE:
          (A) NAME/KEY: modified_base
          (B) LOCATION: 22
          (D) OTHER INFORMATION: /mod_base= um (xi) SEQUENCE DESCRIPTION: SEQ ID NO: 6:

NNNNNNNNNN NNNNNNNNNN NN                                              22

(2) INFORMATION FOR SEQ ID NO: 7:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 7:

CAGGCCCACC CTCCGCAACC                                                 20

(2) INFORMATION FOR SEQ ID NO: 8:

(i) SEQUENCE CHARACTERISTICS:
          (A) LENGTH: 9 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 8:

CTAACCCTA                                                              9

(2) INFORMATION FOR SEQ ID NO: 9:

(i) SEQUENCE CHARACTERISTICS:
          (A) LENGTH: 9 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 9:

CAAACCCAA                                                              9

(2) INFORMATION FOR SEQ ID NO: 10:
```

```
      (i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 10:

CCAACCCCAA                                                             10

(2) INFORMATION FOR SEQ ID NO: 11:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO: 11:

CTCACCCTCA                                                             10

(2) INFORMATION FOR SEQ ID NO: 12:

(i) SEQUENCE CHARACTERISTICS:
          (A) LENGTH: 39 base pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ ID NO: 12:

UAGGGUUACU GAUGAGUCCG UGAGGACGAA ACAAAAAAU                              39

(2) INFORMATION FOR SEQ ID NO: 13:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ ID NO: 13:

UUAGGGUCUG AUGAGUCCGU GAGGACGAAA GACAAAA                                37

(2) INFORMATION FOR SEQ ID NO: 14:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: RNA (xi) SEQUENCE DESCRIPTION: SEQ ID NO: 14:

UCUCAGUCUG AUGAGUCCGU GAGGACGAAA GGGUUA                                 36

(2) INFORMATION FOR SEQ ID NO: 15:

(i) SEQUENCE CHARACTERISTICS:
          (A) LENGTH: 36 base pairs
          (B) TYPE: nucleic acid
          (C) STRANDEDNESS: single
```

(D) TOPOLOGY: linear (ii) MOLECULE TYPE: RNA (xi) SEQUENCE DESCRIPTION: SEQ ID NO: 15:

CCCGAGACUG AUGAGUCCGU GAGGACGAAA CCCGCG                                      36

(2) INFORMATION FOR SEQ ID NO: 16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = 5'-phosphorylated adenine"

(ix) FEATURE:
            (A) NAME/KEY: modified_base
            (B) LOCATION: 20
            (D) OTHER INFORMATION: /mod_base= OTHER
                /note= "N = adenine with 3'-amino
                blocking group"

(xi) SEQUENCE DESCRIPTION: SEQ ID NO: 16:

NTAGCGGCCG CAAGAATTCN                                                       20

(2) INFORMATION FOR SEQ ID NO: 17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 17:

TGAATTCTTG CGGCCGCTAT                                                       20

(2) INFORMATION FOR SEQ ID NO: 18:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: RNA (ix) FEATURE:
            (A) NAME/KEY: modified_base
            (B) LOCATION: 1
            (D) OTHER INFORMATION: /mod_base= um (ix) FEATURE:
            (A) NAME/KEY: modified_base
            (B) LOCATION: 2
            (D) OTHER INFORMATION: /mod_base= um (ix) FEATURE:
            (A) NAME/KEY: modified_base
            (B) LOCATION: 3
            (D) OTHER INFORMATION: /mod_base= OTHER
                /note= "N = 2'-O-methyl-riboadenine"

(ix) FEATURE:

```
        (A) NAME/KEY: modified_base
        (B) LOCATION: 4
        (D) OTHER INFORMATION: /mod_base= gm (ix) FEATURE:
        (A) NAME/KEY: modified_base
        (B) LOCATION: 5
        (D) OTHER INFORMATION: /mod_base= gm (ix) FEATURE:
        (A) NAME/KEY: modified_base
        (B) LOCATION: 6
        (D) OTHER INFORMATION: /mod_base= gm (ix) FEATURE:
        (A) NAME/KEY: modified_base
        (B) LOCATION: 7
        (D) OTHER INFORMATION: /mod_base= um (ix) FEATURE:
        (A) NAME/KEY: modified_base
        (B) LOCATION: 8
        (D) OTHER INFORMATION: /mod_base= um (ix) FEATURE:
        (A) NAME/KEY: modified_base
        (B) LOCATION: 9
        (D) OTHER INFORMATION: /mod_base= OTHER
            /note= "N = 2'-O-methyl-riboadenine"

(ix) FEATURE:
        (A) NAME/KEY: modified_base
        (B) LOCATION: 10
        (D) OTHER INFORMATION: /mod_base= gm (ix) FEATURE:
        (A) NAME/KEY: modified_base
        (B) LOCATION: 11
        (D) OTHER INFORMATION: /mod_base= i (ix) FEATURE:
        (A) NAME/KEY: modified_base
        (B) LOCATION: 12
        (D) OTHER INFORMATION: /mod_base= OTHER
            /note= "N = biotinylated inosine"

(xi) SEQUENCE DESCRIPTION: SEQ ID NO: 18:

NNNNNNNNNN NN                                                           12

(2) INFORMATION FOR SEQ ID NO: 19:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: RNA (ix) FEATURE:
        (A) NAME/KEY: modified_base
        (B) LOCATION: 1
        (D) OTHER INFORMATION: /mod_base= OTHER
            /note= "N = 2'-O-methyl-riboadenine"

(ix) FEATURE:
        (A) NAME/KEY: modified_base
        (B) LOCATION: 2
        (D) OTHER INFORMATION: /mod_base= um (ix) FEATURE:
        (A) NAME/KEY: modified_base
        (B) LOCATION: 3
        (D) OTHER INFORMATION: /mod_base= um (ix) FEATURE:
        (A) NAME/KEY: modified_base
```

```
        (B) LOCATION: 4
        (D) OTHER INFORMATION: /mod_base= gm (ix) FEATURE:
        (A) NAME/KEY: modified_base
        (B) LOCATION: 5
        (D) OTHER INFORMATION: /mod_base= gm (ix) FEATURE:
        (A) NAME/KEY: modified_base
        (B) LOCATION: 6
        (D) OTHER INFORMATION: /mod_base= gm (ix) FEATURE:
        (A) NAME/KEY: modified_base
        (B) LOCATION: 7
        (D) OTHER INFORMATION: /mod_base= um (ix) FEATURE:
        (A) NAME/KEY: modified_base
        (B) LOCATION: 8
        (D) OTHER INFORMATION: /mod_base= um (ix) FEATURE:
        (A) NAME/KEY: modified_base
        (B) LOCATION: 9
        (D) OTHER INFORMATION: /mod_base= OTHER
            /note= "N = 2'-O-methyl-riboadenine"

(ix) FEATURE:
        (A) NAME/KEY: modified_base
        (B) LOCATION: 10
        (D) OTHER INFORMATION: /mod_base= um (ix) FEATURE:
        (A) NAME/KEY: modified_base
        (B) LOCATION: 11
        (D) OTHER INFORMATION: /mod_base= i (ix) FEATURE:
        (A) NAME/KEY: modified_base
        (B) LOCATION: 12
        (D) OTHER INFORMATION: /mod_base= OTHER
            /note= "N = biotinylated inosine"

(xi) SEQUENCE DESCRIPTION: SEQ ID NO: 19:

NNNNNNNNNN NN                                                              12

(2) INFORMATION FOR SEQ ID NO: 20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

GGAAGGTCTG AGACTAG                                                         17

(2) INFORMATION FOR SEQ ID NO: 21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

ATCTCCTGCC CAGTCTG                                                         17
```

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

GAGAAAAACA GCGCGCGGGG AGCAAAAGCA                            30

(2) INFORMATION FOR SEQ ID NO: 23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

GTTTGCTCTA GAATGAACGG TGGAAG                                  26

(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

CACCGGGTTG CGGAGGGAGG                                          20

(2) INFORMATION FOR SEQ ID NO: 25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

GGAGGGGCGA ACGGGCCAGC A                                      21

(2) INFORMATION FOR SEQ ID NO: 26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

TTAGGGTTAG GGTTAGGG                                              18

(2) INFORMATION FOR SEQ ID NO: 27:

(i) SEQUENCE CHARACTERISTICS:

```
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 27:

CAACGAACGG CCAGCAGCTG ACATT                                              25

(2) INFORMATION FOR SEQ ID NO: 28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = 5' phosphorylated adenosine"

(xi) SEQUENCE DESCRIPTION: SEQ ID NO: 28:

NTAGCGGCCG CTTGCCTTCA                                                    20

(2) INFORMATION FOR SEQ ID NO: 29:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 29:

AGAAAAACAG CGCGCGGGGA GCAAAGCA                                           28

(2) INFORMATION FOR SEQ ID NO: 30:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 30:

TCTAACCCTA ACTGAGAAGG GCGTAG                                             26

(2) INFORMATION FOR SEQ ID NO: 31:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 31:

CUAACCCUA                                                                 9
```

(2) INFORMATION FOR SEQ ID NO: 32:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 32:

CCAACCCCA    9

(2) INFORMATION FOR SEQ ID NO: 33:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 33:

CCCAAACCCA AACCCAA    17

(2) INFORMATION FOR SEQ ID NO: 34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 34:

ACCCAAACCC AAACCCAAAC CCAA    24

(2) INFORMATION FOR SEQ ID NO: 35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 35:

CCCCAACCCC AACCCCAA    18

(2) INFORMATION FOR SEQ ID NO: 36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 36:

CCAACCCCAA CCCCAACC    18

(2) INFORMATION FOR SEQ ID NO: 37:

(i) SEQUENCE CHARACTERISTICS:
        (A) LENGTH: 18 base pairs

```
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 37:

TTTCCCTTTC CCTTTCCC                                                 18

(2) INFORMATION FOR SEQ ID NO: 38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 38:

CCAACCCCAA CCCCAACCTT TCCC                                          24

(2) INFORMATION FOR SEQ ID NO: 39:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 39:

TTAGGGTTAG GG                                                       12

(2) INFORMATION FOR SEQ ID NO: 40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 40:

CUCAGUUAGG GUUAGACAAA                                               20

(2) INFORMATION FOR SEQ ID NO: 41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 41:

CGCCCUUCUC AGUUAGGGUU AG                                            22

(2) INFORMATION FOR SEQ ID NO: 42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear
```

-continued

```
    (ii) MOLECULE TYPE: RNA (xi) SEQUENCE DESCRIPTION: SEQ ID NO: 42:

GGCGCCUACG CCCUUCUCAG UU                                                    22
```

MAMMALIAN TELOMERASE

CROSS-REFERENCE TO RELATED APPLICATIONS

This application is a continuation of U.S. patent application Ser. No. 09/057,351, filed 8 Apr. 1998, now U.S. Pat. No. 6,548,298, which is a continuation of U.S. patent application Ser. No. 08/472,802, filed 7 Jun. 1995, now U.S. Pat. No. 5,958,680, which is a continuation-in part of U.S. patent application Ser. No. 08/330,123, filed 27 Oct. 1994, now U.S. Pat. No. 5,583,016, which is a continuation-in-part of U.S. patent application Ser. No. 08/272,102, filed 7 Jul. 1994, abandoned, each of which is incorporated herein by reference.

BACKGROUND OF THE INVENTION

1. Field of Invention

The present invention relates to human telomerase, a ribonucleoprotein enzyme involved in human telomere DNA synthesis. The invention provides methods and compositions relating to the fields of molecular biology, chemistry, pharmacology, and medical and diagnostic technology.

2. Description of Related Disclosures

The DNA at the ends or telomeres of the chromosomes of eukaryotes usually consists of tandemly repeated simple sequences. Telomerase is a ribonucleoprotein enzyme that synthesizes one strand of the telomeric DNA using as a template a sequence contained within the RNA component of the enzyme. See Blackburn, 1992, *Annu. Rev. Biochem.* 61:113-129, incorporated herein by reference.

The RNA component of human telomerase has not been reported in the scientific literature to date, although human telomerase is known to synthesize telomeric repeat units with the sequence 5'-TTAGGG-3'. See Morin, 1989, *Cell* 59:521-529, and Morin, 1991, *Nature* 353:454-456, incorporated herein by reference. This knowledge has not been sufficient to enable the isolation and identification of the remainder of the nucleotide sequence of the RNA component of human telomerase. The RNA component of the telomerase enzymes of *Saccharomyces cerevisiae*, certain species of *Tetrahymena*, as well as that of other ciliates, such as Euplotes and Glaucoma, has been sequenced and reported in the scientific literature. See Singer and Gottschling, Oct. 21, 1994, *Science* 266:404-409; Lingner et al., 1994, *Genes & Development* 8:1984-1988; Greider and Blackburn, 1989, *Nature* 337:331-337; Romero and Blackburn, 1991, *Cell* 67:343-353; and Shippen-Lentz and Blackburn, 1990, *Science* 247:546-552, each of which is incorporated herein by reference. The telomerase enzymes of these ciliates synthesize telomeric repeat units distinct from that in humans.

There is a great need for more information about human telomerase. Despite the seemingly simple nature of the repeat units of telomeric DNA, scientists have long known that telomeres have an important biological role in maintaining chromosome structure and function. More recently, scientists have speculated that loss of telomeric DNA may act as a trigger of cellular senescence and aging and that regulation of telomerase may have important biological implications. See Harley, 1991, *Mutation Research* 256:271-282, incorporated herein by reference.

Methods for detecting telomerase activity, as well as for identifying compounds that regulate or affect telomerase activity, together with methods for therapy and diagnosis of cellular senescence and immortalization by controlling telomere length and telomerase activity, have also been described. See PCT patent publication No. 93/23572, published Nov. 25, 1993, and U.S. patent application Ser. No. 08/315,216; inventors Michael D. West, Jerry Shay, and Woodring Wright), filed Sep. 28, 1994; Ser. No. 08/315,214; inventors Nam Woo Kim, Scott Weinrich, and Calvin B. Harley), filed Sep. 28, 1994; Ser. No. 08/288,501, filed Aug. 10, 1994; Ser. No. 08/014,838, filed Feb. 8, 1993; Ser. Nos. 08/153,051 and 08/151,477, each filed Nov. 12, 1993; Ser. No. 08/060,952, filed May 13, 1993; Ser. No. 08/038,766, filed Mar. 24, 1993; and Ser. No. 07/882,438, filed May 13, 1992, each of which is incorporated herein by reference.

Significant improvements to and new opportunities for telomerase-mediated therapies and telomerase assays and screening methods could be realized if nucleic acid comprising the RNA component and/or encoding the protein components of telomerase were available in pure or isolatable form and the nucleotide sequences of such nucleic acids were known. The present invention meets these and other needs and provides such improvements and opportunities.

SUMMARY OF THE INVENTION

In a first aspect, the present invention provides the RNA component of, as well as the gene for the RNA component of, human telomerase in substantially pure form, as well as nucleic acids comprising all or at least a useful portion of the nucleotide sequence of the RNA component of human telomerase. The present invention also provides RNA component nucleic acids from other species, which nucleic acids share substantial homology with the RNA component of human telomerase, including but not limited to, the RNA components of mammals, such as primates. Other useful nucleic acids of the invention include nucleic acids with sequences complementary to the RNA component; nucleic acids with sequences related to but distinct from nucleotide sequences of the RNA component and which interact with the RNA component or the gene for the RNA component or the protein components of human telomerase in a useful way; and nucleic acids that do not share significant sequence homology or complementarity to the RNA component or the gene for the RNA component but act on the RNA component in a desired and useful way. As described more fully below, the nucleic acids of the invention include both DNA and RNA molecules and modified analogues of either and serve a variety of useful purposes.

Thus, one type of useful nucleic acid of the invention is an antisense oligonucleotide, a triple helix-forming oligonucleotide, or other oligonucleotide or oligonucleotide mimetic (e.g., antisense PNA) that can be used in vivo or in vitro to inhibit the activity of human telomerase. Such oligonucleotides can block telomerase activity in a number of ways, including by preventing transcription of the telomerase gene (for instance, by triple helix formation) or by binding to the RNA component of telomerase in a manner that prevents a functional ribonucleoprotein telomerase from assembling or prevents the RNA component, once assembled into the telomerase enzyme complex, from serving as a template for telomeric DNA synthesis. Typically, and depending on mode of action, these oligonucleotides of the invention comprise a specific sequence of from about 10 to about 25 to 200 or more nucleotides that is either identical or complementary to a specific sequence of nucleotides in the RNA component of telomerase or the gene for the RNA component of telomerase.

Another type of useful nucleic acid of the invention is a ribozyme able to cleave specifically the RNA component of human telomerase, rendering the enzyme inactive. Yet another type of useful nucleic acid of the invention is a probe or primer that binds specifically to the RNA component of human telomerase and so can be used, e.g., to detect the presence of telomerase in a sample. Finally, useful nucleic acids of the invention include recombinant expression plasmids for producing the nucleic acids of the invention. One especially useful type of such a plasmid is a plasmid used for human gene therapy. Useful plasmids of the invention for human gene therapy come in a variety of types, including not only those that encode antisense oligonucleotides or ribozymes but also those that drive expression of the RNA component of human telomerase or a deleted or otherwise altered (mutated) version of the RNA component of human (or other species with RNA component sequences substantially homologous to the human RNA component) telomerase or the gene for the same.

In a second aspect, the invention provides methods for treating a condition associated with the telomerase activity within a cell or group of cells by contacting the cell(s) with a therapeutically effective amount of an agent that alters telomerase activity in that cell. Such agents include the telomerase. RNA component-encoding nucleic acids, triple helix-froming oligonucleotides, antisense oligonucleotides, ribozymes, and plasmids for human gene therapy described above. In a related aspect, the invention provides pharmaceutical compositions comprising these therapeutic agents together with a pharmaceutically acceptable carrier or salt.

In a third aspect, the invention provides diagnostic methods for determining the level, amount, or presence of the RNA component of human telomerase, telomerase, or telomerase activity in a cell, cell population, or tissue sample, or an extract of any of the foregoing. In a related aspect, the present invention provides useful reagents for such methods (including the primers and probes noted above), optionally packaged into kit form together with instructions for using the kit to practice the diagnostic method.

In a fourth aspect, the present invention provides recombinant telomerase preparations and methods for producing such preparations. Thus, the present invention provides a recombinant human telomerase that comprises the protein components of human telomerase as well as the protein components of telomerase from a mammalian species with an RNA component substantially homologous to the RNA component of human telomerase in association with a recombinant RNA component of the invention. Such recombinant RNA component molecules of the invention include those that differ from naturally occurring RNA component molecules by one or more base substitutions, deletions, or insertions, as well as RNA component molecules identical to a naturally occurring RNA component molecule that are produced in recombinant host cells. The method for producing such recombinant telomerase molecules comprises transforming a eukaryotic host cell that expresses the protein components of telomerase with a recombinant expression vector that encodes an RNA component molecule of the invention, and culturing said host cells transformed with said vector under conditions such that the protein components and RNA component are expressed and assemble to form an active telomerase molecule capable of adding sequences (not necessarily the same sequence added by native telomerase) to telomeres of chromosomal DNA.

In a fifth aspect, the invention provides methods for purifying the protein components of human telomerase as well as the protein components of telomerase from a mammalian species with an RNA component substantially homologous to the RNA component of human telomerase. The present invention also provides methods for isolating and identifying nucleic acids encoding such protein components. In related aspects, the present invention provides purified human telomerase and purified telomerase of mammalian species with an RNA component substantially homologous to the RNA component of human telomerase, as well as purified nucleic acids that encode one or more components of such telomerase preparations. The present invention also provides pharmaceutical compositions comprising as an active ingredient the protein components of telomerase or a nucleic acid that encodes or interacts with a nucleic acid that encodes a protein component of telomerase.

The present invention also provides a method for diagnosing a disease (e.g., neoplasia) in a human patient, wherein a diagnostic assay (e.g., determination of hTR) is used to determine if a predetermined pathognomonic concentration of hTR RNA is present in cells in a biological sample from a human patient; if the assay indicates the presence of a pathognomonic amount of hTR outside of the normal range (e.g., beyond the predetermined pathognomonic concentration), the patient is diagnosed as having a disease condition or predisposition.

In a variation of the invention, polynucleotides of the invention are employed for diagnosis of pathological conditions or genetic disease that involve neoplasia, aging, or other medical conditions related to telomerase function, and more specifically conditions and diseases that involve alterations in the structure or abundance of a hTR RNA of hTR gene sequence, or which are linked to a pathognomonic hTR allele which can be detected by RFLP and/or allele-specific PCR, or other suitable detection method.

The invention also provides antisense polynucleotides complementary to hTR polynucleotide sequences, typically complementary to polynucleotide sequences which are substantially identical to a naturally-occurring mammalian hTR gene sequence. Such antisense polynucleotides are employed to inhibit transcription and/or stability and/or functionality of the hTR RNA species and thereby effect a reduction in the amount of the respective telomerase activity in a cell (e.g., a neoplastic cell of a patient). Such antisense polynucleotides can function as telomerase-modulating agents by inhibiting the formation of functional (catalytically active and high fidelity) telomerase holoenzyme required for correct telomere replication and repair in a cell. Antisense polynucelotides can be combined with other antineoplastic therapeutic modalities, such as ionizing radiation or chemotherapy (e.g., with a DNA-damaging agent such as bleomycin, cisplatin, nitrogen mustard, doxyrubicin, nucleotide analogs, and the like). The antisense polynucleotides can promote cell death in susceptible cells (e.g., replicating cells requiring telomerase activity for DNA repair or replication). The hTR antisense polynucleotides are substantially identical to at least 25 contiguous nucleotides of the complementary sequence of the hTR RNA sequence disclosed herein. The hTR antisense polynucleotides are typically ssDNA, ssRNA, methylphosphonate backbone nucleic acids, phosphorothiolate backbone, polyamide nucleic acids, and the like antisense structures known in the art. In one aspect of the invention, an antisense polynucleotide is administered to inhibit transcription and/or activity of of hTR and telomerase in a cell, such as a replicable human cell.

The invention also provides hTR polynucleotide probes for diagnosis of disease states (e.g., neoplasia or preneoplasia) by detection of a hTR RNA or hTR gene rearrangements or amplification of the hTR gene in cells explanted from a patient, or detection of a pathognomonic hTR allele (e.g., by RFLP or allele-specific PCR analysis). Typically, the detection will be by in situ hybridization using a labeled (e.g., $^{32}$P, $^{35}$S, $^{14}$C, $^{3}$H, fluorescent, biotinylated, digoxigeninylated)

antisense polynucleotide complementary to hTR, although Northern blotting, dot blotting, or solution hybridization on bulk RNA or polyA+ RNA isolated from a cell sample may be used, as may PCR amplification using hTR-specific primers. Cells which contain an altered amount (typically a significant increase) of hTR RNA as compared to non-neoplastic cells of the same cell type(s) will be identified as candidate diseased cells. Similarly, the detection of pathognomonic rearrangements or amplification of the hTR gene locus or closely linked loci in a cell sample will identify the presence of a pathological condition or a predisposition to developing a pathological condition (e.g., cancer, genetic disease). The polynucleotide probes are also used for forensic identification of individuals, such as for paternity testing or identification of criminal suspects or unknown decedents.

The present invention also provides a method for diagnosing a disease (e.g., neoplasia) in a human patient, wherein a diagnostic assay (e.g., in situ polynucleotide hybridization of fixed cells by a labelled hTR probe that specifically binds human hTR RNA or gene sequences) is used to determine if a predetermined pathognomonic concentration of hTR RNA is present in a biological sample from a human patient; if the assay indicates the presence of hTR RNA outside of the normal range (e.g., beyond the predetermined pathognomonic concentration), the patient is diagnosed as having a disease condition or predisposition.

The invention also provides therapeutic agents which inhibit neoplasia or apoptosis by modulating telomerase function by inhibiting or augmenting formation of hTR RNA; such agents can be used as pharmaceuticals. Such pharmaceuticals will be used to treat a variety of human and veterinary diseases, such as: neoplasia, hyperplasia, neurodegenerative diseases, aging, AIDS, fungal infection, and the like. In an embodiment, the agent consists of a gene therapy vector capable of transcribing a hTR RNA sequence or its complement, or alternatively an enzymatically inactive hTR RNA which can competitively inhibit formation of functional telomerase holoenzyme.

Other features and advantages of the invention will be apparent from the following description of the drawings, preferred embodiments of the invention, the examples, and the claims.

DEFINITIONS

The term "hTR polynucleotide" as used herein refers to a polynucleotide of at least 20 nucleotides wherein the polynucleotide comprises a segment of at least 20 nucleotides which: are at least 85 percent identical to a naturally-occurring hTR RNA sequence Some hTR polynucleotides having sequence variations as compared to a naturally-occurring hTR sequence can be suitable as hybridization probes, PCR primers, LCR amplimers, and the like.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length hTR gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 25 contiguous nucleotide positions wherein a polynucleotide sequence may be compared to a reference sequence of at least 25 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 89 to 95 percent sequence identity, more usually at least 99 percent sequence identity as compared to a reference sequence over a comparison window of at least 20 nucleotide positions, frequently over a window of at least 30-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length hTR gene sequence as disclosed herein.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance.

As used herein the terms "pathognomonic concentration", "pathognomonic amount", and "pathognomonic hybridization pattern" refer to a concentration, amount, or localization pattern, respectively, of a hTR mRNA in a sample, that indicates the presence of a pathological (e.g., neoplastic, senescent, immunodeficient, neurodegenerative, inflammatory, etc.) condition or a predisposition to developing a neoplastic disease, such as carcinoma, sarcoma, or leukemia. A pathognomonic amount is an amount of hTR RNA in a cell or cellular sample that falls outside the range of normal clinical values that is established by prospective and/or retrospective statistical clinical studies. Generally, an individual having a neoplastic disease (e.g., carcinoma, sarcoma, or leukemia) will exhibit an amount of hTR RNA in a cell or tissue sample that is outside the range of concentrations that characterize normal, undiseased individuals; typically the pathognomonic concentration is at least about one standard deviation outside the mean normal value, more usually it is at least about two standard deviations or more above the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

As used herein, the term "disease allele" refers to an allele of a gene which is capable of producing a recognizable disease. A disease allele may be dominant or recessive and may produce disease directly or when present in combination with a specific genetic background or pre-existing pathological condition. A disease allele may be present in the gene pool or may be generated de novo in an individual by somatic mutation.

The term "antineoplastic agent" is used herein to refer to agents that have the functional property of inhibiting a development or progression of a neoplasm in a human, often including inhibition of metastasis or metastatic potential.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous. A structural gene (e.g., a HSV tk gene) which is operably linked to a polynucleotide sequence corresponding to a transcriptional regulatory sequence of an endogenous gene is generally expressed in substantially the same temporal and cell type-specific pattern as is the naturally-occurring gene.

As used herein, the term "transcriptional unit" or "transcriptional complex" refers to a polynucleotide sequence that comprises a structural gene (exons), a cis-acting linked promoter and other cis-acting sequences necessary for efficient transcription of the structural sequences, distal regulatory elements necessary for appropriate tissue-specific and developmental transcription of the structural sequences, and additional cis sequences important for efficient transcription and translation (e.g., polyadenylation site, mRNA stability controlling sequences).

DESCRIPTION OF PREFERRED EMBODIMENTS

Figure 1:
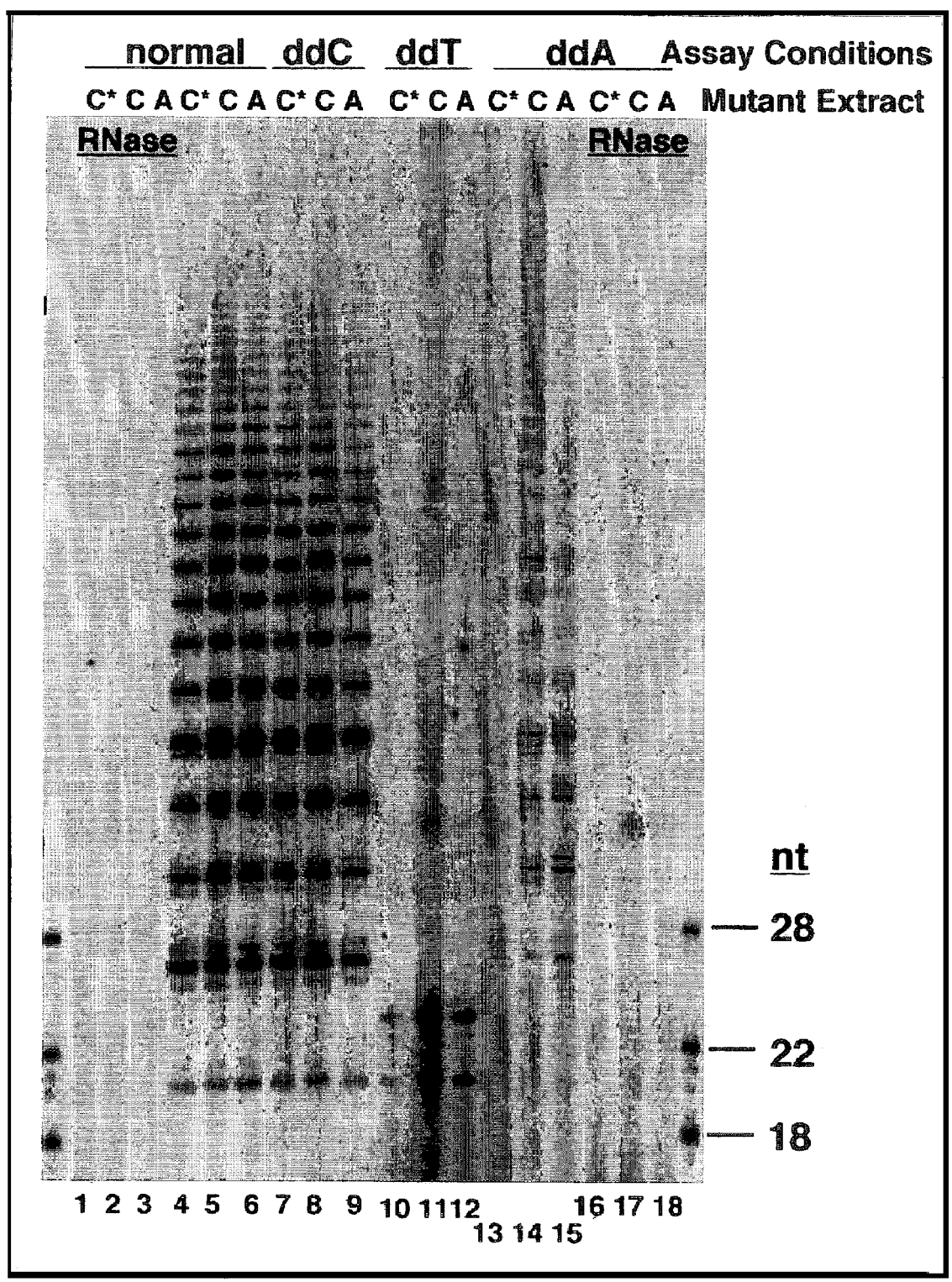
FIG. 1. Telomerase activity from cells expressing template-mutated TRC3 DEAE-sepharose fractionated extracts from mutant TRC-3-expressing stable transformants were assayed for telomerase activity using conventional assays under various reaction conditions. Extracts from cells expressing MuC+17 TRC-3 (lanes 1, 4, 7, 10, 13, 16 labeled C*), MuC TRC-3 (lanes 2, 5, 8, 11, 14, 17 labeled C), or MuA TRC-3 (lanes 3, 6, 9, 12, 15, 18 labeled A) were assayed under normal reaction conditions (lanes 1-6), normal plus 0.5 mM ddCTP (lanes 7-9), normal minus dTTP plus 0.5 mM ddTTP (lanes 10-12), or normal minus dATP plus 0.5 mM ddATP (lanes 13-18). Assay reactions in lanes 1-9 contained 8 μM total dGTP, 1 μM of which was $^{32}$P-dGTP (800 Ci/mmol). To facilitate mutant telomerase detection, assay reactions in lanes 10-18 contained 8 μM total dGTP, 2 μM of which was $^{32}$P-dGTP (800 Ci/mmol). Extracts were treated with DNase-free RNase (25 μg/ml for 10 min at 30° C.) prior to telomerase assays (lanes 1-3, 16-18). Flanking lanes contain DNA markers with sizes in nucleotides (nt) as indicated.

The present invention provides methods, reagents, and pharmaceutical compositions relating to the ribonucleoprotein human telomerase. The invention in part arises out of the cloning and isolation of the RNA component of human telomerase and the gene for that RNA component. The nucleotide sequence of the RNA component of human telomerase is shown below. For convenience, the sequence is shown using the standard abbreviations for ribonucleotides (A is riboadenine, G is riboguanine, C is ribocytidine, and U is uridine). Those of skill in the art recognize that the sequence shown below SEQ ID NO: 1 also shows the sequence of the cDNA, in which the ribonucleotides are replaced by deoxyribonucleotides (with uridine being replaced by thymidine).

than the ⁻560 nucleotide sequence shown above and in fact may comprise more than 1000 nucleotides. However, a fully functional telomerase molecule can be assembled from transcripts consisting of the ⁻560 nucleotide sequence shown above. The 3'-end of the RNA component in native telomerase is believed to lie within the region defined by nucleotides 514-559 in the sequence above; one analysis suggests that the 3'-end may be the U residue at nucleotide 538. Recombinant RNA component molecules comprising less than nucleotides 1-559 of the sequence shown above can also be used to prepare active telomerase.

The cloning of the RNA component of human telomerase required a novel method involving negative selection and cycles of positive selection, described below. Initially, however, an attempt was made to clone the RNA component using reverse transcription and a method for cloning the ends of cDNA called "5'-RACE" PCR amplification. The reverse transcription reaction was initiated with a primer identical to the repeat unit in the single-strand portion of human telomeric DNA and thus complementary to a sequence believed to be present in the RNA component of human telomerase. The primer also comprised, at its 5'-end, a sequence corresponding to a restriction enzyme recognition site. However, when the cDNA produced by the reverse transcription reaction and PCR amplification was examined by gel electrophoresis and nucleotide sequence analysis of the bands of nucleic acid present in the gel, only ribosomal RNA sequences were detected. Similar problems were encountered when variations of this 5'-RACE approach were attempted using nested primers.

The successful cloning effort began with the preparation of cDNA from purified preparations of human telomerase as well as from cell lines that have human telomerase activity

```
GGGUUGCGGA GGGUGGGCCU GGGAGGGGUG GUGGCCAUUU UUUGUCUAAC  50

CCUAACUGAG AAGGGCGUAG GCGCCGUGCU UUUGCUCCCC GCGCGCUGUU 100

UUUCUCGCUG ACUUUCAGCG GGCGGAAAAG CCUCGGCCUG CCGCCUUCCA 150

CCGUUCAUUC UAGAGCAAAC AAAAAAUGUC AGCUGCUGGC CCGUUCGCCC 200

CUCCCGGGGA CCUGCGGCGG GUCGCCUGCC CAGCCCCCGA ACCCCGCCUG 250

GAGGCCGCGG UCGGCCCGGG GCUUCUCCGG AGGCACCCAC UGCCACCGCG 300

AAGAGUUGGG CUCUGUCAGC CGCGGGUCUC UCGGGGGCGA GGGCGAGGUU 350

CAGGCCUUUC AGGCCGCAGG AAGAGGAACG GAGCGAGUCC CCGCGCGCGG 400

CGCGAUUCCC UGAGCUGUGG GACGUGCACC CAGGACUCGG CUCACACAUG 450

CAGUUCGCUU UCCUGUUGGU GGGGGGAACG CCGAUCGUGC GCAUCCGUCA 500

CCCCUCGCCG GCAGUGGGGG CUUGUGAACC CCCAAACCUG ACUGACUGGG 550

CCAGUGUGCU                                             560
```

The sequence above is shown in the 5'-3' direction and is numbered for reference. The template sequence of the RNA component is believed to be located within the region defined by nucleotides 50-60 (5'-CUAACCCUAAC-3') (SEQ ID NO: 2), which is complementary to a telomeric sequence composed of about one-and-two-thirds telomeric repeat units.

This sequence was derived from cDNA clones and from the genomic clone of the RNA component. When the RNA component is first transcribed from the corresponding gene, at least some of the RNA transcripts produced are much longer and from cell lines that do not have detectable human telomerase activity. The method used to prepare the cDNA is described in detail in Example 1, below. Two negative selection steps and successive cycles of positive selection were used in conjunction with the cDNA preparations from the two human cell lines to lower the concentration of unwanted sequences and to raise the concentration of the desired RNA component sequences.

The negative selection steps involved the preparation of biotinylated PCR product from cDNA prepared from a human cell line that does not have detectable telomerase activity. The biotinylated PCR product was denatured and then rehybridized in a solution comprising a much lower concentration of non-biotinylated PCR product (100 biotinylated product: 1 non-biotinylated product) from cDNA prepared from a human cell line that does have telomerase activity. Given the possibility that the telomerase negative cell line might contain some low amount of the RNA component, the hybridization step was conducted to discriminate or select against only RNA expressed abundantly in both cell lines. After hybridization to a $C_ot$ selected to allow hybridization of the most abundantly expressed RNA, the unwanted material was removed by binding to streptavidinylated magnetic particles; the supernatant remaining after particle collection contained the desired cDNA for the RNA component of human telomerase. The process for PCR amplification of cDNA is described in Example 2, below.

This material was further enriched for the desired cDNA by successive cycles of positive selection. In the positive selection step, a biotinylated probe complementary to the predicted template sequence in the RNA component of human telomerase was hybridized to PCR product from an enriched (by negative selection) sample of the PCR-amplified cDNA from a human cell line that has telomerase activity. After hybridization, the probe/target complexes were bound to avidinylated magnetic beads, which were then collected and used as a source of nucleic acid enriched in RNA component sequences in further cycles of positive selection. The positive selection process is described in more detail in Examples 3 and 4, below.

After the third cycle of positive selection, the amplification products were separated by gel electrophoresis, and sections of the gel corresponding to nucleic acids ⁻200 bp in size were removed. The nucleic acids were then eluted from the gel sections and amplified by PCR. The PCR amplification products were digested with restriction enzyme NotI and then inserted by ligation into the NotI site of plasmid pBluescriptIISK+, commercially available from Stratagene. The resulting plasmids were transformed into E. coli host cells, and individual colonies were isolated and used as a source of nucleic acid for further analysis and DNA sequencing. Individual colonies were grown in the wells of a 96-well microtiter plate, which was then used as a master plate, and blots of DNA from the colonies in the plate were prepared and hybridized to a probe comprising a telomeric repeat sequence and therefore complementary to the RNA component of human telomerase. A number of clones positive by this test were then analyzed by DNA sequencing and a variety of other tests.

These other tests included the following: (1) determination whether antisense oligonucleotides complementary to the putative RNA component would inhibit telomerase activity in human cell extracts known to contain telomerase; (2) determination whether PCR primers specific for a putative RNA component clone sequence could be used to amplify a nucleic acid present in a telomerase sample and whether the product observed, if any, would track telomerase activity during purification of telomerase; and (3) determination whether PCR primers specific for a putative RNA component clone sequence could be used to amplify a nucleic acid present in greater abundance in cell extracts from cells in which telomerase activity is known to be high (i.e., tumor cells) than in cell extracts from cells known to produce no or only low amounts of telomerase activity. One clone, designated plasmid pGRN7, produced results in these tests consistent with the determination that the plasmid comprised cDNA corresponding to the RNA component of human telomerase.

Thus, antisense oligonucleotides corresponding to sequences of the putative RNA component sequence of pGRN7 exhibited inhibition of telomerase activity in vitro. Likewise, when telomerase was purified from cell extracts by a process involving (1) DEAE chromatography; (2) Sephadex S300 chromatography; and (3) either glycerol gradient, SP sepharose, or phenyl sepharose separation and fractions collected, PCR primers specific for the putative RNA component sequence of pGRN7 amplified a nucleic acid of the appropriate size, and the amount of amplification product correlated well with the amount of telomerase activity observed in the fractions collected. Finally, cell extracts from normal (no detectable telomerase activity) and cancer (telomerase activity present), as well as testis (telomerase activity present), cells showed corresponding amounts of PCR product upon reverse transcription and PCR amplification (RT-PCR) with primers specific for the putative RNA component comprised in pGRN7. The protocol for the RT-PCR is described in Examples 5 and 6, below.

The above results provided convincing evidence that the RNA component of human telomerase had been cloned, so plasmid pGRN7 was then used to isolate a genomic clone for the RNA component from a human cell line, as described in Example 7, below. The genomic clone was identified in and isolated from a genomic library of human DNA inserted into a lambda vector FIXII purchased from Stratagene. The desired clone comprising the RNA component gene sequences contained an ⁻15 kb insert and was designated clone 28-1. This clone has been deposited with the American Type Culture Collection and is available under the accession No. ATCC 75925. Lambda clone 28-1 was deposited under the Budapest Treaty on Oct. 25, 1994 at the American Type Culture Collection, Rockville, Md. 20852. Various restriction fragments were subcloned from this phage and sequenced. The gene has also been localized to the distal end of the q arm of chromosome 3. The sequence information obtained from a SauIIIA1 restriction enzyme recognition site at one end of the ⁻15 kb insert to an internal HindIII restriction enzyme recognition site, which comprises all of the mature RNA component sequence as well as transcription control elements of the RNA component gene, of lambda clone 28-1 is shown below (SEQ ID NO:3) using the standard deoxyribonucleotide abbreviations and depicted in the 5'-3' direction.

```
GATCAGTTAG AAAGTTACTA GTCCACATAT AAAGTGCCAA GTCTTGTACT    50

CAAGATTATA AGCAATAGGA ATTTAAAAAA AGAAATTATG AAAACTGACA   100

AGATTTAGTG CCTACTTAGA TATGAAGGGG AAAGAAGGGT TTGAGATAAT   150

GTGGGATGCT AAGAGAATGG TGGTAGTGTT GACATATAAC TCAAAGCATT   200

TAGCATCTAC TCTATGTAAG GTACTGTGCT AAGTGCAATA GTGCTAAAAA   250
```

-continued

```
CAGGAGTCAG ATTCTGTCCG TAAAAAACTT TACAACCTGG CAGATGCTAT  300
GAAAGAAAAA GGGGATGGGA GAGAGAGAAG GAGGGAGAGA GATGGAGAGG  350
GAGATATTTT ACTTTTCTTT CAGATCGAGG ACCGACAGCG ACAACTCCAC  400
GGAGTTTATC TAACTGAATA CGAGTAAAAC TTTTAAGATC ATCCTGTCAT  450
TTATATGTAA AACTGCACTA TACTGGCCAT TATAAAAATT CGCGGCCGGG  500
TGCGGTGGCT CATACCTGTA ATCCCAGCAC TTTGGGAGGC CGAAGCGGGT  550
GGATCACTTG AGCCCTGGCG TTCGAGACCA GCCTGGGCAA CATGGTGAAA  600
CCCCCGTCTC TACTAAAAAC ACAAAAACTA GCTGGGCGTG GTGGCAGGCG  650
CCTGTAATCC CAGCTACTCA GGAGGCTGAG ACACGAGAAT CGCTTGAACC  700
CGGGAGCAGA GGTTGCAGTG AGCCGAGATC ACGCCACTAG ACTCCATCCA  750
GCCTGGGCGA AAGAGCAAGA CTCCGTCTCA AAAAAAAAAA TCGTTACAAT  800
TTATGGTGGA TTACTCCCCT CTTTTTACCT CATCAAGACA CAGCACTACT  850
TTAAAGCAAA GTCAATGATT GAAACGCCTT TCTTTCCTAA TAAAAGGGAG  900
ATTCAGTCCT TAAGATTAAT AATGTAGTAG TTACACTTGA TTAAAGCCAT  950
CCTCTGCTCA AGGAGAGGCT GGAGAAGGCA TTCTAAGGAG AAGGGGGCAG 1000
GGTAGGAACT CGGACGCATC CCACTGAGCC GAGACAAGAT TCTGCTGTAG 1050
TCAGTGCTGC CTGGGAATCT ATTTTCACAA AGTTCTCCAA AAAATGTGAT 1100
GATCAAAACT AGGAATTAGT GTTCTGTGTC TTAGGCCCTA AAATCTTCCT 1150
GTGAATTCCA TTTTTAAGGT AGTCGAGGTG AACCGCGTCT GGTCTGCAGA 1200
GGATAGAAAA AAGGCCCTCT GATACCTCAA GTTAGTTTCA CCTTTAAAGA 1250
AGGTCGGAAG TAAAGACGCA AAGCCTTTCC CGGACGTGCG GAAGGGCAAC 1300
GTCCTTCCTC ATGGCCGGAA ATGGAACTTT AATTTCCCGT TCCCCCCAAC 1350
CAGCCCGCCC GAGAGAGTGA CTCTCACGAG AGCCGCGAGA GTCAGCTTGG 1400
CCAATCCGTG CGGTCGGCGG CCGCTCCCTT TATAAGCCGA CTCGCCCGGC 1450
AGCGCACCGG GTTGCGGAGG GTGGGCCTGG GAGGGGTGGT GGCCATTTTT 1500
TGTCTAACCC TAACTGAGAA GGGCGTAGGC GCCGTGCTTT TGCTCCCCGC 1550
GCGCTGTTTT TCTCGCTGAC TTTCAGCGGG CGGAAAAGCC TCGGCCTGCC 1600
GCCTTCCACC GTTCATTCTA GAGCAAACAA AAAATGTCAG CTGCTGGCCC 1650
GTTCGCCCCT CCCGGGGACC TGCGGCGGGT CGCCTGCCCA GCCCCGAAC  1700
CCCGCCTGGA GGCCGCGGTC GGCCCGGGGC TTCTCCGGAG GCACCCACTG 1750
CCACCGCGAA GAGTTGGGCT CTGTCAGCCG CGGGTCTCTC GGGGGCGAGG 1800
GCGAGGTTCA GGCCTTTCAG GCCGCAGGAA GAGGAACGGA GCGAGTCCCG 1850
GCGCGCGGCG CGATTCCCTG AGCTGTGGGA CGTGCACCCA GGACTCGGCT 1900
CACACATGCA GTTCGCTTTC CTGTTGGTGG GGGAACGCC  GATCGTGCGC 1950
ATCCGTCACC CCTCGCCGGC AGTGGGGGCT TGTGAACCCC CAAACCTGAC 2000
TGACTGGGCC AGTGTGCTGC AAATTGGCAG GAGACGTGAA GGCACCTCCA 2050
AAGTCGGCCA AAATGAATGG GCAGTGAGCC GGGGTTGCCT GGAGCCGTTC 2100
CTGCGTGGGT TCTCCCGTCT TCCGCTTTTT GTTGCCTTTT ATGGTTGTAT 2150
TACAACTTAG TTCCTGCTCT GCAGATTTTG TTGAGGTTTT TGCTTCTCCC 2200
AAGGTAGATC TCGACCAGTC CCTCAACGGG GTGTGGGGAG AACAGTCATT 2250
```

```
                                 -continued
TTTTTTTGAG AGATCATTTA ACATTTAATG AATATTTAAT TAGAAGATCT 2300

AAATGAACAT TGGAAATTGT GTTCCTTTAA TGGTCATCGG TTTATGCCAG 2350

AGGTTAGAAG TTTCTTTTTT GAAAAATTAG ACCTTGGCGA TGACCTTGAG 2400

CAGTAGGATA TAACCCCCAC AAGCTT                            2426
```

The RNA component sequence begins at base 1459. A variety of transcription control elements can also be identified in the sequence. An A/T Box consensus sequence is found at nucleotides 1438-1444; PSE consensus sequences are found at nucleotides 1238-1250 as well as nucleotides 1406-1414; a CAAT box consensus sequence is found at nucleotides 1399-1406; an SP1 consensus sequence is found at nucleotides 1354-1359; and a beta-interferon response element consensus sequence is found at nucleotides 1234-1245.

The plasmids described above that were constructed during the cloning of the RNA component of human telomerase and the gene for the RNA component are important aspects of the present invention. These plasmids can be used to produce the RNA component of, as well as the gene for, human telomerase in substantially pure form, yet another important aspect of the present invention. In addition, those of skill in the art recognize that a variety of other plasmids, as well as non-plasmid nucleic acids in substantially pure form, that comprise all or at least a useful portion of the nucleotide sequence of the RNA component of human telomerase are useful materials provided by the present invention.

As a general point regarding the nucleic acids and preparations containing the same of the invention, those of skill in the art recognize that the nucleic acids of the invention include both DNA and RNA molecules, as well as synthetic, non-naturally occurring analogues of the same, and heteropolymers of deoxyribonucleotides, ribonucleotides, and/or analogues of either. The particular composition of a nucleic acid or nucleic acid analogue of the invention will depend upon the purpose for which the material will be used and the environment(s) in which the material will be placed. Modified or synthetic, non-naturally occurring nucleotides, have been designed to serve a variety of purposes and to remain stable in a variety of environments, such as those in which nucleases are present, as is well known in the art. Modified or synthetic non-naturally occurring nucleotides, as compared to the naturally occurring ribo- or deoxyribonucucleotides, may differ with respect to the carbohydrate (sugar), phosphate linkage, or base portions, of the nucleotide, or may even contain a non-nucleotide base (or no base at all) in some cases. See, e.g., Arnold et al., PCT patent Publication No. WO 89/02439, entitled "Non-nucleotide Linking Reagents for Nucleotide Probes" incorporated herein by reference.

Just as the nucleic acids of the invention can comprise a wide variety of nucleotides, so too can those nucleic acids serve a wide variety of useful functions. One especially useful type of nucleic acid of the invention is an antisense oligonucleotide that can be used in vivo or in vitro to inhibit the activity of human telomerase. Antisense oligonucleotides comprise a specific sequence of from about 10 to about 25 to 200 or more (i.e., large enough to form a stable duplex but small enough, depending on the mode of delivery, to administer in vivo, if desired) nucleotides complementary to a specific sequence of nucleotides in the RNA component of human telomerase. The mechanism of action of such oligonucleotides can involve binding of the RNA component either to prevent assembly of the functional ribonucleoprotein telomerase or to prevent the RNA component from serving as a template for telomeric DNA synthesis.

Illustrative antisense oligonucleotides of the invention that serve to inhibit telomerase activity in vivo and/or in vitro include the oligonucleotides mentioned above in connection with the tests to determine whether clone pGRN7 comprised the cDNA for the RNA component of human telomerase. Three such oligonucleotides were synthesized as 2'-O-methyl RNA oligonucleotides, which bind more tightly to RNA than DNA oligonucleotides and are more resistant to hydrolysis than unmodified RNA oligonucleotides, and, as noted above, were used to demonstrate inhibition of telomerase activity in vitro. The sequence of each of these O-methyl RNA oligonucleotides is shown below.

T3    5'-CUCAGUUAGGGUUAGACAAA-3'

P3    5'-CGCCCUUCUCAGUUAGGGUUAG-3'

TA3   5'-GGCGCCUACGCCCUUCUCAGUU-3'

These oligonucleotides can also be used to inhibit telomerase activity in human cells.

Those of skill in the art will recognize that the present invention provides a wide variety of antisense oligonucleotides able to inhibit telomerase activity. Another useful antisense oligonucleotides of the invention is oligonucleotide Tel-AU, which has the sequence 5'-CAGGCCCACCCTC-CGCAACC-3' (SEQ ID NO:7, and which, like any of the antisense oligonucleotides of the invention, can be synthesized using phosphorothioate nucleotides, chiral-methyl phoshponates, naturally occurring nucleotides, or mixtures of the same to impart stability and the desired $T_m$. Those of skill in the art recognize that a wide variety of modified nucleotide analogues, such as O-methyl ribonucleotides, phosphorothioate nucleotides, and methyl phosphonate nucleotides, can be used to produce nucleic acids of the invention with more desired properties (i.e., nuclease-resistant, tighter-binding, etc.) than those produced using naturally occurring nucleotides. Other techniques for rendering oligonucleotides nuclease-resistant include those described in PCT patent publication No. 94/12633.

Additional embodiments directed to modulation of telomerase activity include methods that employ specific antisense polynucleotides complementary to all or part of the human telomerase RNA component (hTR) sequences, such as antisense polynucleotides to the human hTR gene or its transcribed RNA, including truncated forms which may be associated with telomerase holoenzyme. Such complementary antisense polynucleotides may include nucleotide substitutions, additions, deletions, or transpositions, so long as specific binding to the relevant target sequence corresponding to hTR or its gene is retained as a functional property of the polynucleotide. Complementary antisense polynucleotides include soluble antisense RNA or DNA oligonucleotides which can hybridize specifically to hTR RNA species and prevent transcription of the hTR gene (Ching et al. (1989)

Proc. Natl. Acad. Sci. U.S.A. 86: 10006; Broder et al. (1990) Ann. Int. Med. 113: 604; Loreau et al. (1990) FEBS Letters 274: 53; Holcenberg et al., WO91/11535; U.S. Ser. No. 07/530,165; WO91/09865; WO91/04753; WO90/13641; and EP 386563, each of which is incorporated herein by reference). The antisense polynucleotides therefore inhibit production of functional hTR. Since hTR expression (transcription rate and/or RNA stability) is associated with activation and enzymatic activity of telomerase holoenzyme, antisense polynucleotides that prevent transcription of RNA corresponding to hTR and/or the interaction of hTR to the protein component of human telomerase and/or the interaction of hTR to telomeric sequences may inhibit telomerase activity and/or reverse a phenotype, such as immortalization or neoplastic transformation, of cells expressing telomerase activity in the absence of antisense polynucelotides. Compositions containing a therapeutically effective dosage of hTR antisense polynucleotides may be administered for treatment of diseases which require telomerase activity for cellular pathogenesis (e.g., neoplasia) or to inhibit gamete production or maintenence (i.e., as a contraceptive), if desired. Antisense polynucleotides of various lengths may be produced, although such antisense polynucleotides typically comprise a sequence of about at least 25 consecutive nucleotides which are substantially complementary to a naturally-occurring hTR polynucleotide sequence, and typically which are perfectly complementary to a human hTR sequence, often being complementary to the sequence of hTR which is complementary to the telomere repeat sequence, or complementary to a portion of the hTR which contacts the telomerase polypeptide subunit.

Antisense polynucleotides may be produced from a heterblogous expression cassette in a transfectant cell or transgenic cell. Alternatively, the antisense polynucleotides may comprise soluble oligonucleotides that are administered to the external milieu, either in the culture medium in vitro or in interstitial spaces and bodily fluids (e.g., blood, CSF) for application in vivo. Soluble antisense polynucleotides present in the external milieu have been shown to gain access to the cytoplasm and inhibit specific RNA species. In some embodiments the antisense polynucleotides comprise methylphosphonate moieties, C-5 propynyl moieties, 2' fluororibose sugars, or are polyamide nucleic acids (PNAs) (Egholm et al. (1992) *J. Am. Chem. Soc.* 114: 1895; Wittung et al. (1994) *Nature* 368: 561; Egholm et al. (1993) *Nature* 365: 566; Hanvey et al. (1992) *Science* 258: 1481, incorporated herein by reference). For general methods relating to antisense polynucleotides, see *Antisense RNA and DNA*, (1988), D. A. Melton, Ed., Cold Spring Harbor Laboratory, Cold Spring Harbor, N.Y.).

In addition to the antisense oligonucleotides of the invention, one can construct oligonucleotides that will bind to duplex nucleic acid either in the folded RNA component or in the gene for the RNA component, forming a triple helix-containing or triplex nucleic acid to inhibit telomerase activity. Such oligonucleotides of the invention are constructed using the base-pairing rules of triple helix formation and the nucleotide sequence of the RNA component (Cheng et al. (1988) *J. Biol. Chem.* 263: 15110; Ferrin and Camerini-Otero (1991) *Science* 354: 1494; Ramdas et al. (1989) *J. Biol. Chem.* 264: 17395; Strobel et al. (1991) *Science* 254: 1639; Hsieh et al. (1990) op.cit.; Rigas et al. (1986) *Proc. Natl. Acad. Sci. (U.S.A.)* 83: 9591, incorporated herein by reference). Such oligonucleotides can block telomerase activity in a number of ways, including by preventing transcription of the telomerase gene or by binding to a duplex region of the RNA component of telomerase in a manner that prevents the RNA component either from forming a functional ribonucleoprotein telomerase or from serving as a template for telomeric DNA synthesis. Typically, and depending on mode of action, the triplex-forming oligonucleotides of the invention comprise a specific sequence of from about 10 to about 25 to 200 or more (i.e., large enough to form a stable triple helix but small enough, depending on the mode of delivery, to administer in vivo, if desired) nucleotides "complementary" (in this context, complementary means able to form a stable triple helix) to a specific sequence in the RNA component of telomerase or the gene for the RNA component of telomerase.

In addition to the antisense and triple helix-forming oligonucleotides of the invention, "sense" oligonucleotides identical in sequence to at least a portion of the RNA component of human telomerase can also be used to inhibit telomerase activity. Oligonucleotides of the invention of this type are characterized in comprising either (1) less than the complete sequence of the RNA component needed to form a functional telomerase enzyme or (2) the complete sequence of the RNA component needed to form a functional telomerase enzyme as well as a substitution or insertion of one or more nucleotides that render the resulting RNA non-functional. In both cases, inhibition of telomerase activity is observed due to the "mutant" RNA component binding the protein components of human telomerase to form an inactive telomerase molecule. The mechanism of action of such oligonucleotides thus involves the assembly of a non-functional ribonucleoprotein telomerase or the prevention of assembly of a functional ribonucleoprotein telomerase. Sense oligonucleotides of the invention of this type typically comprise a specific sequence of from about 20, 50 200, 400, 500, or more nucleotides identical to a specific sequence of nucleotides in the RNA component of human telomerase.

Thus, another useful oligonucleotide of the invention comprises an altered or mutated sequence of the RNA component of human telomerase. Yu et al., 1990, *Nature* 344: 126, shows that a mutated form of the RNA component of *Tetrahymena* telomerase can be incorporated into the telomerase of *Tetrahymena* cells and that the incorporation has deleterious effects on those cells. Incorporation of mutated forms of the RNA component of human telomerase may have similar effects on human cells that otherwise have telomerase activity without affecting normal human cells that do not have telomerase activity. Such mutated forms include those in which the sequence 5'-CTAACCCTA-3' (SEQ ID NO:8) is mutated to 5'-CAAACCCAA-3' (SEQ ID NO:9), 5'-CCAACCCCAA-3' (SEQ ID NO:10), or 5'-CTCACCCTCA-3'(SEQ ID NO:11). Each of these altered RNA component sequences alters the telomeric repeat units incorporated into the chromosomal DNA, thus affecting chromosome structure and function. Such oligonucleotides can be designed to contain restriction enzyme recognition sites useful in diagnostic methods for the presence of the altered RNA component via restriction enzyme digestion of telomeric DNA or an extended telomerase substrate.

To illustrate this aspect of the invention, site-specific mutagenesis was carried out using a plasmid (designated pGRN33, available from the American Type Culture Collection under accession No. ATCC 75925) that comprises an ~2.5 kb HindIII-SacI fragment from lambda clone 28-1 (see Example 7, below) as well as the SV40 origin of replication (but no promoter activity). The resulting plasmids, designated pGRN34 (comprising 5'-CAAACCCAA-3' SEQ ID NO:9), pGRN36 (comprising 5'-CCAACCCCAA-3' SEQ ID NO:10), and pGRN37 (comprising 5'-CTCACCCTCA-3' SEQ ID NO:11), were transformed into eukaryotic host cells (a 293-derived cell line expressing SV40 large T antigen), and telomerase assays were conducted using cell extracts from the transformants.

The assays showed that the telomerase activity in the cells resulted in the formation of nucleic acids comprising the altered sequences, indicating that the genomic clone comprised a functional RNA component gene and that the plasmids comprised an altered but functional RNA component gene. These results illustrate how the present invention provides recombinant telomerase preparations and methods for producing such preparations. The present invention provides a recombinant human telomerase that comprises the protein components of human telomerase in functional association with a recombinant RNA component of the invention. Such recombinant RNA component molecules of the invention include those that differ from naturally occurring RNA component molecules by one or more base substitutions, deletions, or insertions, as well as RNA component molecules identical to a naturally occurring RNA component molecule that are produced in recombinant host cells. The method for producing such recombinant telomerase molecules comprises transforming a eukaryotic host cell that expresses the protein components of telomerase with a recombinant expression vector that encodes an RNA component molecule of the invention, and culturing said host cells transformed with said vector under conditions such that the protein components and RNA component are expressed and assemble to form an active telomerase molecule capable of adding sequences (not necessarily the same sequence added by native telomerase) to telomeres of chromosomal DNA. Other useful embodiments of such recombinant DNA expression vectors (or plasmids) include plasmids that comprise the gene for the RNA component of human telomerase with a deletion, insertion, or other modification that renders the gene nonfunctional. Such plasmids are especially useful for human gene therapy to "knock-out" the endogenous RNA component gene, although a highly efficient transformation and recombination system is required, to render the treated cells irreversibly mortal.

Other oligonucleotides of the invention called "ribozymes" can also be used to inhibit telomerase activity. Unlike the antisense and other oligonucleotides described above, which bind to an RNA, a DNA, or a telomerase protein component, a ribozyme not only binds but also specifically cleaves and thereby potentially inactivates a target RNA, such as the RNA component of human telomerase. Such a ribozyme can comprise 5'- and 3'-terminal sequences complementary to the telomerase RNA. Depending on the site of cleavage, a ribozyme can render the telomerase enzyme inactive. See PCT patent publication No. 93/23572, supra. Those in the art upon review of the RNA sequence of the human telomerase RNA component will note that several useful ribozyme target sites are present and susceptible to cleavage by, for example, a hammerhead motif ribozyme. Illustrative ribozymes of the invention of this type include the ribozymes below, which are RNA molecules having the sequences indicated:

```
1:
5'-UAGGGUUACUGAUGAGUCCGUGAGGACGAAACAAAAAAU-3';

2:
5'-UUAGGGUCUGAUGAGUCCGUGAGGACGAAAGACAAA-3';
```

-continued
```
3:
5'-UCUCAGUCUGAUGAGUCCGUGAGGACGAAAGGGUUA-3'; and

4:
5'-CCCGAGACUGAUGAGUCCGUGAGGACGAAACCCGCG-3'.
```

Other optimum target sites for ribozyme-mediated inhibition of telomerase activity can be determined as described by Sullivan et al., PCT patent publication No. 94/02595 and Draper et al., PCT patent publication No. 93/23569, both incorporated herein by reference. As described by Hu et al., PCT patent publication No. 94/03596, incorporated herein by reference, antisense and ribozyme functions can be combined in a single oligonucleotide. Moreover, ribozymes can comprise one or more modified nucleotides or modified linkages between nucleotides, as described above in conjunction with the description of illustrative antisense oligonucleotides of the invention. In one aspect, a catalytic subunit of RNase P (human or *E. coli*) is modified (see, Altman S (1995) *Biotechnology* 13: 327) to generate a guide sequence which corresponds to the portion of hTR which basepairs to the telomere repeat sequence; such RNase P variants can cleave telomere sequences. In one aspect, a catalytic subunit of RNase P (human or *E. coli*) is modified to generate a guide sequence which is complementary to a portion of hTR such that the RNase P variant can cleave hTR RNA. Such engineered ribozymes can be expressed in cells or can be transferred by a variety of means (e.g., liposomes, immunoliposomes, biolisitics, direct uptake into cells, etc.). Other forms of ribozymes (group I intron ribozymes (Cech T (1995) *Biotechnology* 13; 323); hammerhead ribozymes (Edgington S M (1992) *Biotechnology* 10: 256) can be engineered on the basis of the disclosed hTR sequence information to catalyze cleavage of hTR RNA and/or human telomere repeat sequences.

Thus, the invention provides a wide variety of oligonucleotides to inhibit telomerase activity. Such oligonucleotides can be used in the therapeutic methods of the invention for treating disease, which methods comprise administering to a patient a therapeutically effective dose of a telomerase inhibitor or activator of the invention. One can measure telomerase inhibition or activation to determine the amount of an agent that should be delivered in a therapeutically effective dose using the assay protocols described in the copending U.S. patent applications and PCT patent publication No. 93/23572 noted above. As noted in those applications and discussed above, inhibition of telomerase activity renders an immortal cell mortal, while activation of telomerase activity can increase the replicative lifespan of a cell. Telomerase inhibition therapy is an effective treatment against cancers involving the uncontrolled growth of immortal cells, and telomerase activation is an effective treatment to prevent cell senescence. Delivery of agents that inhibit or block telomerase activity, such as an antisense oligonucleotide, a triple helix-forming oligonucleotide, a ribozyme, or a plasmid that drives expression of a mutant RNA component of telomerase can prevent telomerase action and ultimately leads to cell senescence and cell death of treated cells.

In addition, the present invention provides therapeutic methods that ensure that normal cells remain mortal; for instance, the RNA component can be modified using standard genetic engineering procedures to delete all or a portion of a natural gene encoding the component (e.g., by in vitro mutagenesis) by genetic recombination. Such cells will then be irreversibly mortal. This procedure is useful in gene therapy, where normal cells modified to contain expression plasmids are introduced into a patient, and one wants to ensure cancerous cells are not introduced or, if such cells are introduced, then those cells have been rendered irreversibly mortal.

Because telomerase is active only in tumor, germline, and certain stem cells of the hematopoietic system, other normal cells are not affected by telomerase inhibition therapy. Steps can also be taken to avoid contact of the telomerase inhibitor with germline or stem cells, although this may not be essential. For instance, because germline cells express telomerase activity, inhibition of telomerase may negatively impact spermatogenesis and sperm viability, suggesting that telomerase inhibitors may be effective contraceptives or sterilization agents. This contraceptive effect may not be desired, however, by a patient receiving a telomerase inhibitor of the invention for treatment of cancer. In such cases, one can deliver a telomerase inhibitor of the invention in a manner that ensures the inhibitor will only be produced during the period of therapy, such that the negative impact on germline cells is only transient.

Other therapeutic methods of the invention employ the telomerase RNA nucleic acid of the invention to stimulate telomerase activity and to extend replicative cell life span. These methods can be carried out by delivering to a cell a functional recombinant telomerase ribonucleoprotein of the invention to the cell. For instance, the ribonucleoprotein can be delivered to a cell in a liposome, or the gene for the RNA component of human telomerase (or a recombinant gene with different regulatory elements) can be used in a eukaryotic expression plasmid (with or without sequences coding for the expression of the protein components of telomerase) to activate telomerase activity in various normal human cells that otherwise lack detectable telomerase activity due to low levels of expression of the RNA component or a protein component of telomerase. If the telomerase RNA component is not sufficient to stimulate telomerase activity, then the RNA component can be transfected along with genes expressing the protein components of telomerase to stimulate telomerase activity. Thus, the invention provides methods for treating a condition associated with the telomerase activity within a cell or group of cells by contacting the cell(s) with a therapeutically effective amount of an agent that alters telomerase activity in that cell.

Cells that incorporate extra copies of the telomerase RNA gene can exhibit an increase in telomerase activity and an associated extended replicative life span. Such therapy can be carried out ex vivo on cells for subsequent introduction into a host or can be carried out in vivo. The advantages of stabilizing or increasing telomere length by adding exogenous telomerase genes ex vivo to normal diploid cells include: telomere stabilization can arrest cellular senescence and allow potentially unlimited amplification of the cells; and normal diploid cells with an extended life span can be cultured in vitro for drug testing, virus manufacture, or other useful purposes. Moreover, ex vivo amplified stem cells of various types can be used in cell therapy for particular diseases, as noted above.

Telomere stabilization can also suppress cancer incidence in replicating cells by preventing telomeres from becoming critically short as cells near crisis. During crisis, massive genomic instability is generated as the protective effect of the telomeric cap is lost. The "genetic deck" is reshuffled, and almost all cells die. The rare cells that emerge from this process are typically aneuploid with many gene rearrangements and end up reestablishing stability in their telomeres by expressing telomerase. If crisis can be prevented by keeping telomeres long, then the genomic instability associated with crisis can also be prevented, limiting the chances that an individual cell will suffer the required number of genetic mutations needed to spawn a metastatic cancer.

Cells that can be targeted for telomerase gene therapy (therapy involving increasing the telomerase activity of a target cell) include but are not limited to hematopoietic stem cells (AIDS and post-chemotherapy), vascular endothelial cells (cardiac and cerebral vascular disease), skin fibroblasts and basal skin keratinocytes (wound healing and burns), chondrocytes (arthritis), brain astrocytes and microglial cells (Alzheimer's Disease), osteoblasts (osteoporosis), retinal cells (eye diseases), and pancreatic islet cells (Type I diabetes).

Typically, the therapeutic methods of the invention involve the administration of an oligonucleotide that functions to inhibit or stimulate telomerase activity under in vivo physiological conditions and will be stable under those conditions. As noted above, modified nucleic acids may be useful in imparting such stability, as well as for ensuring delivery of the oligonucleotide to the desired tissue, organ, or cell. Methods useful for delivery of oligonucleotides for therapeutic purposes are described in Inouye et al., U.S. Pat. No. 5,272,065, incorporated herein by reference.

While oligonucleotides can be delivered directly as a drug in a suitable pharmaceutical formulation, one can also deliver oligonucleotides using gene therapy and recombinant DNA expression plasmids of the invention. One such illustrative plasmid is described in Example 8, below. In general, such plasmids will comprise a promoter and, optionally, an enhancer (separate from any contained within the promoter sequences) that serve to drive transcription of an oligoribonucleotide, as well as other regulatory elements that provide for episomal maintenance or chromosomal integration and for high-level transcription, if desired. Adenovirus-based vectors are often used for gene therapy and are suitable for use in conjunction with the reagents and methods of the present invention. See PCT patent publication Nos. 94/12650; 94/12649; and 94/12629. Useful promoters for such purposes include the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), and the constitutive CMV promoter. A plasmid useful for gene therapy can comprise other functional elements, such as selectable markers, identification regions, and other genes. Recombinant DNA expression plasmids can also be used to prepare the oligonucleotides of the invention for delivery by means other than by gene therapy, although it may be more economical to make short oligonucleotides by in vitro chemical synthesis.

In related aspects, the invention features pharmaceutical compositions including a therapeutically effective amount of a telomerase inhibitor or telomerase activator of the invention. Pharmaceutical compositions of telomerase inhibitors of the invention include a mutant RNA component of human telomerase, an antisense oligonucleotide or triple helix-forming oligonucleotide that binds the RNA component or the gene for the same of human telomerase, or a ribozyme able to cleave the RNA component of human telomerase, or combinations of the same or other pharmaceuticals in a pharmaceutically acceptable carrier or salt. Other pharmaceutical compositions of the invention comprise a telomerase activator preparation, such as purified human telomerase or mRNA for the protein components of telomerase and the RNA component of telomerase, and are used to treat senescence-related disease. In an aspect, a mutated sense hTR is administered to a cell population; said mutated sense hTR comprises at least one base mismatch with respect to the human telomerase repeat sequence, but is capable of exhibiting telomerase activity in conjunction with human telomerase polypeptide component, producing misincorporation at selected nucleotide positions in the human telomerase repeat, thereby generating telomeres which rely on the continued presence of the mutated sense hTR for substantial replication. A therapeutic method is provided wherein a mutated sense hTR is administered to a cell population for a sufficient period to introduce telomere sequences which are substantially non-functional as templates for naturally occurring hTR, followed by withdrawal of the mutated sense hTR which results in rapid loss of average telomere length in the cell population and enhanced senescence or cell mortality.

The therapeutic agent can be provided in a formulation suitable for parenteral, nasal, oral, or other mode of administration. See PCT patent publication No. 93/23572, supra.

Diagnostic Methods

The present invention provides diagnostic methods and reagents in addition to the pharmaceutical formulations and therapeutic methods described above. The invention provides diagnostic methods for determining the level, amount, or presence of the RNA component of human telomerase, telomerase, or telomerase activity in a cell, cell population, or tissue sample. In a related aspect, the present invention provides useful reagents for such methods, optionally packaged into kit form together with instructions for using the kit to practice the diagnostic method. As noted above in connection with the tests conducted to determine that clone pGRN7 contained the cDNA for the RNA component of human telomerase, the levels of the RNA component are elevated in tumor cells. Thus, detection of the RNA component is a useful diagnostic for tumor cells.

In addition, probes or primers that bind specifically to the RNA component of human telomerase (or either strand of the gene for the same) can be used in diagnostic methods to detect the presence of telomerase nucleic acid in a sample. Primers and probes are oligonucleotides that are complementary, and so will bind, to a target nucleic acid. Although primers and probes can differ in sequence and length, the primary differentiating factor is one of function: primers serve to initiate DNA synthesis, as in PCR amplification, while probes are typically used only to bind to a target nucleic acid. Typical lengths for a primer or probe can range from 8 to 20 to 30 or more nucleotides. A primer or probe can also be labeled to facilitate detection (i.e., radioactive or fluorescent molecules are typically used for this purpose) or purification/separation (i.e., biotin or avidin is often used for this purpose).

An especially preferred diagnostic method of the invention involves the detection of telomerase RNA component sequences in cell or tissue samples taken from patients suspected to be at risk for cancer. Such methods will typically involve binding a labelled probe or primer to an RNA component sequence under conditions such that only perfectly matched (complementary) sequences bind (hybridize) to one another. Detection of labelled material bound to RNA in the sample will correlate with the presence of telomerase activity and the presence of cancer cells. Some cells may express the RNA component of telomerase but remain telomerase-negative due to lack of expression of the protein components of telomerase. If one desired to detect the presence of telomerase activity in such cells, then one could first isolate protein and then determine whether the protein fraction contains the telomerase RNA component, which would signal the presence of telomerase activity. The diagnostic methods of the invention may be especially useful in detecting the presence of telomerase activity in tissue biopsies and histological sections in which the method is carried out in situ, typically after amplification of telomerase RNA component using specific PCR primers of the invention.

Depending on the length and intended function of the primer, probe, or other nucleic acid comprising sequences from the RNA component of human telomerase, expression plasmids of the invention may be useful. For instance, recombinant production of the full-length RNA component of the invention can be carried out using a recombinant DNA expression plasmid of the invention that comprises a nucleic acid comprising the nucleotide sequence of the RNA component positioned for transcription under the control of a suitable promoter. Host cells for such plasmids can be either prokaryotic or eukaryotic, and the promoter, as well as the other regulatory elements and selectable markers chosen for incorporation into the expression plasmid will depend upon the host cell used for production.

The intact RNA component gene, i.e., the promoter, which includes any regulatory sequences in the 5'-region of the gene, and RNA component coding region, can be used to express the RNA component in human cells, including human cells that have been immortalized by viral transformation or cancer. The promoter of the RNA component gene may be regulated, however, and for this and other reasons, one may want to express the RNA component under the control of a different promoter. On the other hand, the promoter of the RNA component gene can be used independently of the RNA component coding sequence to express other coding sequences of interest. For instance, one could study the transcriptional regulation of the RNA component gene by fusing the promoter of the RNA component gene to a coding sequence for a "reporter" coding sequence, such as the coding sequence for beta-galactosidase or another enzyme or protein the expression of which can be readily monitored. Thus, the promoter and other regulatory elements of the gene for the RNA component of human telomerase can be used not only to express the RNA component but also protein components of human telomerase, antisense or other oligonucleotides, as well as other gene products of interest in human cells. Expression plasmids comprising the intact gene for the RNA component of human telomerase can be especially useful for a variety of purposes, including gene therapy. Those of skill in the art recognize that a wide variety of expression plasmids can be used to produce useful nucleic acids of the invention and that the term "plasmid", as used herein, refers to any type of nucleic acid (from a phage, virus, chromosome, etc.) that can be used to carry specific genetic information into a host cell and maintain that information for a period of time.

As indicated by the foregoing description, access to purified nucleic acids comprising the sequence of the RNA component of human telomerase provides valuable diagnostic and therapeutic methods and reagents, as well as other important benefits. One important benefit of the present invention is that the methods and reagents of the invention can be used to isolate the RNA component and genes for the RNA component of telomerase from any mammalian species that has an RNA component substantially homologous to the human RNA component of the present invention. The phrase "substantially homologous" refers to that degree of homology required for specific hybridization of an oligonucleotide or nucleic acid sequence of the human RNA component to a nucleic acid sequence of an RNA component sequence of another mammalian species. Given such substantial homology, those of ordinary skill in the art can use the nucleic acids and oligonucleotide primers and probes of the invention to identify and isolate substantially homologous sequences.

For instance, one can probe a genomic or cDNA library to detect homologous sequences. One can also use primers corresponding to regions of the RNA component sequence and PCR amplification under low or moderate stringency conditions to amplify a specific homologous nucleic acid sequence from preparations of RNA or DNA from a mammalian species. By using these and other similar techniques, those of ordinary skill can readily isolate not only variant RNA component nucleic acids from human cells but also homologous RNA component nucleic acids from other mammalian cells, such as cells from primates, from mammals of veterinary interest, i.e., cattle, sheep, horse, dogs, and cats, and from rodents, i.e., rats, mice, and hamsters. In turn, these nucleic acids can be used to prepare transgenic animals of great value for screening and testing of pharmaceuticals that regulate telomerase activity. For instance, by using a plasmid of the invention, one can "knock out" the RNA component gene or replace the natural RNA component gene with a recombinant inducible gene in a mus spretus embryonic stem cell and then generate a transgenic mouse that will be useful as a model or test system for the study of age- or senescence-related disease. Example 9, below, illustrates how such methodology has been used to identify and isolate RNA component sequences of primates.

The reagents of the present invention also allow the cloning and isolation of nucleic acids encoding the protein components of human as well as other mammalian telomerase enzymes, which have not previously been available. Access to such nucleic acids provide complementary benefits to those provided by the nucleic acids comprising nucleic acid sequences of the RNA component of human telomerase. For instance, and as noted above, the therapeutic benefits of the present invention can be enhanced, in some instances, by use of purified preparations of the protein components of human telomerase and by access to nucleic acids encoding the same. The nucleic acids of the invention that encode the RNA component of human telomerase can be used to isolate the nucleic acid encoding the protein components of human telomerase, allowing access to such benefits. Thus, the invention provides methods for isolating and purifying the protein components of human telomerase, as well as for identifying and isolating nucleic acids encoding the protein components of human telomerase. In related aspects, the present invention provides purified human telomerase, purified nucleic acids that encode the protein components of human telomerase, recombinant expression plasmids for the protein components of human telomerase. The invention also provides pharmaceutical compositions comprising as an active ingredient either the protein components of human telomerase or a nucleic acid that either encodes those protein components or interacts with nucleic acids that encode those protein components, such as antisense oligonucleotides, triple helix-froming oligonucleotides, ribozymes, or recombinant DNA expression plasmids for any of the foregoing.

The cloned RNA component of human telomerase can be used to identify and clone nucleic acids encoding the protein components of the ribonucleoprotein telomerase enzyme. Several different methods can be employed to achieve identification and cloning of the protein components. For instance, one can use affinity capture of the enzyme or partially denatured enzyme using as an affinity ligand either (1) nucleotide sequences complementary to the RNA component to bind to the RNA component of the intact enzyme; or (2) the RNA component to bind the protein components of a partially or fully denatured enzyme. The ligand can be affixed to a solid support or chemically modified (e.g., biotinylated) for subsequent immobilization on the support. Exposure of cell extracts containing human telomerase, followed by washing and elution of the telomerase enzyme bound to the support, provides a highly purified preparation of the telomerase enzyme. The protein components can then be optionally purified further or directly analyzed by protein sequencing. The protein sequence determined can be used to prepare primers and probes for cloning the cDNA or identifying a clone in a genomic bank comprising nucleic acids that encode a protein component of telomerase.

Affinity capture of telomerase utilizing an engineered RNA component can also be conducted using in vitro transcribed telomerase RNA and a system for the reconstitution of telomerase enzyme activity. See Autexier and Greider, 1994, *Genes & Development* 8:563-575, incorporated herein by reference. The RNA is engineered to contain a tag, similar to epitope tagging of proteins. The tag can be an RNA sequence to which a tightly binding ligand is available, e.g., an RNA sequence-specific antibody, a sequence-specific nucleic acid binding protein, or an organic dye that binds tightly to a specific RNA sequence. The tolerance of telomerase for the tag sequence and position can be tested using standard methods. Synthesis of the altered RNA component and the reconstitution step of this method can also be carried out in vivo. Affinity capture using the immobilized ligand for the RNA tag can then be used to isolate the enzyme.

Expression screening can also be used to isolate the protein components of the telomerase enzyme. In this method, cDNA expression libraries can be screened with labeled telomerase RNA, and cDNAs encoding proteins that bind specifically to telomerase RNA can be identified. A molecular genetic approach using translational inhibition can also be used to isolate nucleic acids encoding the protein components of the telomerase enzyme. In this method, telomerase RNA sequences will be fused upstream of a selectable marker. When expressed in a suitable system, the selectable marker will be functional. When cDNA encoding a telomerase RNA binding protein is expressed, the protein will bind to its recognition sequence thereby blocking translation of the selectable marker, thus allowing for identification of the clone encoding the protein. In other embodiments of this method, the blocked translation of the selectable marker will allow transformed cells to grow. Other systems that can be employed include the "interaction trap system" described in PCT patent publication No. WO 94/10300; the "one-hybrid" system described in Li and Herskowitz, Dec. 17, 1993, *Science* 262:1870-1874, and Zervos et al., Jan. 29, 1993, *Cell* 72:223-232; and the "two-hybrid" system commercially available from Clontech.

Telomerase RNA binding or telomerase activity assays for detection of specific binding proteins and activity can be used to facilitate the purification of the telomerase enzyme and the identification of nucleic acids that encode the protein components of the enzyme. For example, nucleic acids comprising RNA component sequences can be used as affinity reagents to isolate, identify, and purify peptides, proteins or other compounds that bind specifically to a sequence contained within the RNA component, such as the protein components of human telomerase. Several different formats are available, including gel shift, filter binding, footprinting, Northwestern (RNA probe of protein blot), and photo-crosslinking, to detect such binding and isolate the components that bind specifically to the RNA component. These assays can be used to identify binding proteins, to track purification of binding proteins, to characterize the RNA binding sites, to determine the molecular size of binding proteins, to label proteins for preparative isolation, and for subsequent immunization of animals for antibody generation to obtain antibodies for use in isolating the protein or identifying a nucleic acid encoding the protein in a coupled transcription/translation system.

As will be apparent to those of skill in the art upon reading of this disclosure, the present invention provides valuable reagents relating to human telomerase, as well as a variety of useful therapeutic and diagnostic methods. The above description of necessity provides a limited sample of such methods, which should not be construed as limiting the scope of the invention. Other features and advantages of the invention will be apparent from the following examples and claims.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. H A Erlich, Freeman Press, New York, N.Y. (1992); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; PCR, eds. McPherson, Quirkes, and Taylor, IRL Press, Oxford; and U.S. Pat. No. 4,683,202, which are incorporated herein by reference).

hTr polynucleotides and their complements may serve as hybridization probes or primers for detecting RNA or DNA sequences of hTR. For such hybridization and PCR applications may contain substantial deletions, additions, nucleotide substitutions and/or transpositions, so long as specific hybridization or specific amplification of a hTR sequence is retained. However, such nucleotide substitutions, deletions, and additions should not substantially disrupt the ability of the polynucleotide to hybridize to a hTR RNA or hTR gene sequence under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a hTR RNA or hTR genomic gene sequence, wherein the probe preferentially hybridizes to the specific target such that, for example, a single band corresponding to one or more of the RNA species of the hTR gene (or specifically cleaved or processed hTR RNA species) can be identified on a Northern blot of RNA prepared from a suitable cell source (e.g., a somatic cell expressing hTR RNA). Polynucleotides of the invention which specifically hybridize to hTR or human telomeric sequences may be prepared on the basis of the sequence data provided herein according to methods and thermodynamic principles known in the art and described in Maniatis et al., *Molecular Cloning: A Laboratory Manual*, 2nd Ed., (1989), Cold Spring Harbor, N.Y. and Berger and Kimmel, *Methods in Enzymology, Volume 152, Guide to Molecular Cloning Techniques* (1987), Academic Press, Inc., San Diego, Calif., which are incorporated herein by reference.

Within the human population there can be minor alterations in the basic primary sequence of hTR, including allelic variants, restriction site polymorphisms, and congenital hTR disease alleles associated with genetic disease.

If desired, PCR amplimers for amplifying substantially full-length hTR copies may be selected at the discretion of the practioner. Similarly, amplimers to amplify portions of the hTR gene or RNA may be selected.

Gene Therapy

Transferring exogenous genetic material into cells (i.e., DNA-mediated transfection) is an essential method for basic research in cell biology and molecular genetics, as well as the basis for developing effective methods for human gene therapy. So far, the majority of the approved gene transfer trials in the United States rely on replication-defective retroviral vectors harboring a therapeutic polynucleotide sequence as part of the retroviral genome (Miller et al. (1990) *Mol. Cell. Biol.* 10: 4239; Kolberg R (1992) *J. NIH Res.* 4: 43; Cornetta et al. (1991) *Hum. Gene Ther.* 2: 215). Adenoviral vectors have also been described for potential use in human gene therapy (Rosenfeld et al. (1992) *Cell* 68: 143).

The other gene transfer method that has been approved for use in humans is physical transfer of plasmid DNA in liposomes directly into tumor cells in situ. Unlike viral vectors which must be propagated in cultured cells, plasmid DNA can be purified to homogeneity and thus reduces the potential for pathogenic contamination. In some situations (e.g., tumor cells) it may not be necessary for the exogenous DNA to stably integrate into the transduced cell, since transient expression may suffice to kill the tumor cells. Liposome-mediated DNA transfer has been described by various investigators (Wang and Huang (1987) *Biochem. Biophys. Res. Commun.* 147: 980; Wang and Huang (1989) *Biochemistry* 28: 9508; Litzinger and Huang (1992) *Biochem. Biophys. Acta* 1113: 201; Gao and Huang (1991) *Biochem. Biophys. Res. Commun.* 179: 280; Felgner WO91/17424; WO91/16024).

Immunoliposomes have also been described as carriers of exogenous polynucleotides (Wang and Huang (1987) *Proc. Natl. Acad. Sci. (U.S.A.)* 84: 7851; Trubetskoy et al. (1992) *Biochem. Biophys. Acta* 1131: 311). Immunoliposomes hypothetically might be expected to have improved cell type specificity as compared to liposomes by virtue of the inclusion of specific antibodies which presumably bind to surface antigens on specific cell types. Behr et al. (1989) *Proc. Natl. Acad. Sci. (U.S.A.)* 86: 6982 report using lipopolyamine as a reagent to mediate transfection itself, without the necessity of any additional phospholipid to form liposomes.

Accordingly, a polynucleotide substantially identical to at least 25 nucleotides, preferably 50 to 100 nucelotides or more, of the hTR sequence or its complement, is operably linked to a heterologous promoter to form a transcription unit capable of expressing an hTR RNA or an antisense hTR RNA in a human cell. Such a transcription unit may be comprised in a transgene, adenoviral vector, or other gene therapy modality for delivery into human cells, such as for therapy of a telomerase-related disease (e.g., neoplasia). Suitable delivery methods of the hTR sense or antisense expression construct will be selected by practitioners in view of acceptable practices and regulatory requirements.

The following examples describe specific aspects of the invention to illustrate the invention and provide a description of the methods used to isolate and identify the RNA component of human telomerase for those of skill in the art. The examples should not be construed as limiting the invention, as the examples merely provide specific methodology useful in understanding and practice of the invention.

Example 1

Preparation of PCR-amplifiable cDNA

RNA was obtained from 293 cells by guanidine-thiocyanate extraction or from purified telomerase fractions by phenol/chloroform extractions. The total RNA from 293 cells was size fractionated on a 2% agarose gel, and the RNA below 500 bp was isolated.

First strand cDNA synthesis was performed with Superscript™ II reverse transcriptase obtained from Bethesda Research Laboratories (BRL). About 0.5 to 1.0 µg RNA was mixed with about 40 ng of random primer (6 mer) in water at a total volume of 11 µl. The solution was heated for 10 min. at 95° C. and then cooled on ice for 5-10 min. The denatured nucleic acid was collected by centrifugation. The denatured RNA and primer mixture were then resuspended by adding, in the order shown: 4 µl 5×1st strand synthesis buffer; 2 µl 0.1 M dithiothreitol (DTT); 1 µl RNAsin (Pharmacia); and 1 µl dNTP (0.125 mM each for 0.5 mM total concentration). The reaction mixture was incubated at 42° C. for 1 min., and then, 1 µl (200 units) of Superscript™ II RTase (BRL) was added and mixed into the reaction, which was then incubated for 60 min. at 42° C. The resulting reaction mixture, containing the newly synthesized cDNA was placed on ice until second strand synthesis was performed.

Second strand cDNA synthesis was performed as follows. About 20 µl of the reaction mixture from the first strand cDNA synthesis reaction mixture (from above) was mixed with, in the order shown, the following components: 111.1 µl of water; 16 µl of 10× E. coli DNA ligase buffer; 3 µl of dNTP (2.5 mM each stock); 1.5 µl of E. coli DNA ligase (15 units from BRL); 7.7 µl of E. coli DNA polymerase (40 units from Pharmacia); and 0.7 µl of E. coli RNase H (BRL). The resulting solution was gently mixed and incubated for 2 hours at 16° C., at which time 1 µl (10 units) of T4 DNA polymerase was added to the reaction tube and incubation continued for 5 min. at the same temperature (16° C.). The reaction was stopped, and the nucleic acid was collected by extracting the reaction with phenol/chloroform twice, precipitating the nucleic acid with ethanol, and centrifuging the reaction mixture to pellet the nucleic acid.

The cDNA pellet collected by centrifugation was resuspended in 20 µl of TE buffer and ligated to a double-stranded oligonucleotide called "NotAB" composed of two oligonucleotides (NH2 is an amino blocking group):

NotA: 5'-pATAGCGGCCGCAAGAATTCA-NH2 (SEQ ID NO:16

NotB: 5'-TGAATTCTTGCGGCCGCTAT-3' (SEQ ID NO:17

The double-stranded oligonucleotide was made by mixing 50 µl of NotA oligonucleotide (100 pmol) with 50 µl of NotB oligonucleotide (100 pmol) in 46.25 µl of water, heating the resulting solution for 5 min. at 95° C., and adding 3.75 µl of 20×SSC buffer while the solution was still hot. The tube containing the mixture was then placed in a beaker containing hot water (at a temperature of about 70 to 75° C.), the temperature of which was allowed to drop slowly to below 15° C., so that the two oligonucleotides could hybridize to form the double-stranded oligonucleotide NotAB. The resulting nucleic acid was collected by precipitation and centrifugation.

The double-stranded NotAB oligonucleotide was resuspended in about 30 µl TE buffer and then ligated to the cDNA in a reaction mixture containing 10 µl of the cDNA preparation described above, about 50 pmol (calculated by OD260) of NotAB; 2 µl of 10×T4 DNA ligase buffer; 1.2 µl of T4 DNA ligase; 0.2 µl of 10 mM ATP; and water in a total volume of 20 µl by incubating the reaction mixture at 16° C. overnight. The reaction was then heat-inactivated by heating the reaction mixture for 10 min. at 65° C. About 1 to 2 µl of the resulting mixture was typically used for PCR amplification; one can amplify the ligation mixture for 10 to 15 cycles (94° C., 45 seconds; 60° C., 45 seconds; and 72° C., 1.5 min.) and save as a stock, as described in Example 2.

Example 2

PCR Amplification of cDNA

The cDNA was routinely amplified by preparing an amplification reaction mixture composed of 5 µl of 10×PCR buffer (500 mM KCl; 100 mM Tris, pH=8.3; and 20 mM MgCl$_2$; 5-8 µl of dNTP (2.5 mM each); 1 µl of Taq polymerase (Boehringer-Mannheim); 0.1 µl of gene 32 protein (Boehringer-Mannheim); 6 µl of Not B primer (20 µM stock); 2 µl of the cDNA (prepared as described in Example 1), and water to 50 µl. This mixture was then overlayed with 50 to 100 µl of mineral oil, and PCR amplification was performed for 10 to 15 cycles of 94° C., 45 seconds; 60° C., 45 seconds; and 72° C., 1.5 min. After amplification, the reaction mixture was extracted with phenol/chloroform, and the amplified nucleic acid was precipitated with ethanol and collected by centrifugation. The precipitate was then dissolved in 100 µl of TE buffer to prepare a stock solution.

Example 3

PCR Amplification for Cyclic Selection

To make PCR product for cyclic selection, about 1 µl of a stock solution prepared as described in Example 2 was amplified in 50 µl of PCR reaction mixture prepared as described in Example 2, except that 21-24 cycles of primer annealing, extension, and denaturation of product were conducted. After amplification, reaction mixtures were extracted with phenol/chloroform, precipitated with ethanol, and collected by centrifugation. Product yield was estimated by staining with ethidium bromide after agarose gel electrophoresis of a small aliquot of the reaction mixture. Typically, about 2 µg of the nucleic acid product were used for cyclic selection.

After cyclic selection, described in Example 4, about 1 to 2 µl of the selected "pull-down" products (out of a total volume of 20 µl) were PCR amplified as described in Example 2 for 22 cycles, precipitated with ethanol, and collected by centrifugation in preparation for further cyclic selection.

Example 4

Positive Selection of PCR-amplified cDNA

For the positive selection step of the cyclic selection process used to clone the RNA component of human telomerase, about 2 µg of the PCR-amplified cDNA were diluted into 25 µl of TE buffer and then mixed with 1.25 µl of 20×SSC and the resulting solution heated to 95° C. for 3 min. The temperature was lowered to 60° C. for 5 min., and one µl (0.1 µg/µl) of the R2 or R4 biotinylated probe was added. The sequences of these probes are shown below. The probes are O-methyl-RNA probes, so U is O-methyl-uridine, A is O-methyl-riboadenine, G is O-methyl-riboguanine, and I is inosine.

```
R2:         5'-UUAGGGUUAGII-biotin

R4:         5'-AUUGGGUUAUII-biotin
```

The R2 probe is specific for the telomere repeat, and the R4 probe is specific for RNase P, which was used to track the effectiveness and efficiency of the cyclic selection process. By carrying out a cyclic selection simultaneously but separately for RNase P RNA, a molecule of known sequence, one can have greater confidence that the cyclic selection process is functioning properly with respect to the molecule of interest, in this case the RNA component of human telomerase. After either the R2 or R4 probe was added to the mixture at 65° C., the temperature of the hybridization reaction mixture was lowered to 30° C. by incubating the mixture at that temperature for 5 min., and then the reaction mixtures were further lowered to a temperature of 14° C. by incubating at that temperature for 60 min. Finally, the mixture was incubated at 4° C. for 2-12 hours.

The entire hybridization reaction mixture for each sample (R2 or R4) was added to 400 µl of 0.5×SSC at 4° C. and then added to a tube of ice-cold magnetic beads, which were purchased from Promega and pre-washed four times with 0.5×SSC before use. The resulting mixture was incubated 30 min. at 4° C. to ensure complete binding to the magnetic beads. Each reaction tube was then incubated briefly at room temperature on the magnetic stand (Promega) to pull down the beads. The beads were resuspended in cold 0.5×SSC (600 µl) and placed (in a tube) on ice. The samples were washed three more times with 0.5×SSC in this manner. Nucleic acid was eluted from the beads by resuspending the beads in 100 µl of water and incubating for 2 min. at 65° C. before placing the beads back on the magnetic stand for collection. This process was repeated three more times; the last time, the resuspended beads were incubated for 5 min. at 65° C. before placing the beads on the magnetic stand for collection. All of the 100 µl supernatants (for each sample) were pooled and dried down to 20 µl in a SpeedVac™ centrifuge. The recovered DNA was then PCR amplified for another round of amplification and selection. After each amplification, the PCR products were phenol-chloroform extracted twice, ethanol precipitated, and resuspended in 20 µl of TE buffer.

Typically, PCR amplifications were verified by agarose gel electrophoresis. In addition, a variety of controls were used to monitor the cyclic selection process. As one control, PCR "arms" (oligonucleotides of defined sequence that serve as primer hybridization sites) were placed on a nucleic acid that comprised a neomycin resistance-conferring gene. The resulting nucleic acid was mixed with the PCR-amplified cDNA and monitored at each selection by quantitative PCR. As another control, RNase P was followed in both the RNase P selected and the telomerase RNA component selected libraries.

Example 5

RT-PCR Protocol

The first strand cDNA was made in substantial accordance with the procedure described in Example 1. Basically, RNA was purified from each telomerase fraction containing 0.1 to 1 µg RNA; typical, about one-third to one-fifth of the RNA made from a 300 µl fraction was used. The RNA was mixed with 40 to 80 ng random hexamer in 10 µl, denatured for 10 min. at 95° C. (using a thermal-cycling instrument), and chilled on ice. The denatured RNA and 6-mer were added to a reaction mixture containing 4 µl of 5×1st strand synthesis buffer supplied by the manufacturer of the reverse transcriptase (RTase, purchased from BRL), 2 µl of 0.1 M DTT, 1 µl of 10 mM dNTP (each), 1 µl of RNase inhibitor (Pharmacia), and water to a total volume of 9 µl. The combined mixture was placed into a 42° C. water bath. After 1-2 min. incubation, 1 µl of Superscript™ II RTase (BRL) was added to the mixture. The incubation was continued for 60 min. at 42° C. The reaction was stopped by heating the tube for 10 min. at 95-98° C. The first strand cDNA was collected by brief centrifugation, aliquoted to new tubes, quickly frozen on dry ice, and stored at −80° C. or used immediately.

Example 6

PCR Amplification of cDNA with a Specific Primer Set

For a 20 µl PCR reaction with radioactively labeled nucleotides, 1 µl of the cDNA prepared in accordance with the procedure of Example 5 was mixed with 20 pmol of primer 1, 20 pmol of primer 2, 2.5 µl of 2.5 mM dNTP, 5 µCi of alpha-$^{32}$P-dATP, 2 units of Taq polymerase (Boehringer-Mannheim), 0.2 µg of T4 gene 32 protein (Boehringer-Mannheim), 2 µl of 10×buffer (500 mM KCl, 100 mM Tris-HCl-pH8.3, and 20 mM $MgCl_2$), and water to a total volume of 20 µl. One drop of mineral oil was then added to the tube.

The PCR amplification conditions for the telomerase RNA component clone were: 94° C. for 45 sec., 60° C. for 45 sec., 72° C. for 1.5 min. The number of cycles differed depending on the type of purified materials used for RNA preparation but typically range from 18 to 25 cycles. As for all quantitative RT-PCR, several reactions with differing cycles were run for each sample to determine when the PCR amplification became saturated and non-linear.

For the RNase P used as a control, the PCR amplification conditions were: 94° C. for 45 sec., 50° C. for 45 sec., and 72° C. for 1.5 min. Again, the number of cycles ranged from 15 to 22 cycles, depending on the nature of the samples. The sequences of the primers used for RNase P amplification are shown below:

```
P3:         5'-GGAAGGTCTGAGACTAG-3'

P4:         5'-ATCTCCTGCCCAGTCTG-3'
```

The PCR product obtained with these two primers is about 110 bp in size.

After PCR, the products (5 to 10 µl of the reaction mixture) were loaded onto a 6% native polyacrylamide gel and electrophoresed. After electrophoresis, the gel was dried and exposed to a PhosphorImager cassette or to autoradiographic film for analysis.

Example 7

Cloning the Gene for the RNA Component of Human Telomerase

The procedures used to clone the gene for the RNA component of human telomerase were carried out as generally described in Maniatis et al., *Laboratory Molecular Cloning Manual*. A genomic DNA library of DNA from the human lung fibroblast cell line WI-38 inserted into phage lambda vector FIXII was purchased from Stratagene. The phage were plated at a concentration of about 25,000 plaques per plate onto three sets of 15 (150 mm) plates. The plates were made with NZY agar and NZY top agarose; the cells used for the phage transformation were XL1BlueMRAP2 cells; and the transformants were grown overnight for about 16 hours at 37° C. The plates were then chilled at 4° C. for about an hour, and then the plaques were "lifted" onto C/P nylon circles (filter paper from Bio Rad). This process was repeated to produce a duplicate set of lifted filters. The filters (in duplicate) were denatured, neutralized, equilibrated in 6×SSC buffer, exposed to UV irradiation to cross-link the nucleic acid to the filter, and then dried on blotter paper.

Prehybridization was conducted for one hour at 37° C. in 50% formamide buffer. The filters were probed with an ⁻218 bp, radioactively-labeled, NotI fragment from clone pGRN7, which had been isolated by electroelution from a 5% polyacrylamide gel after separation by electrophoresis and then nick-translated with alpha-$^{32}$P-dCTP using a nick-translation kit from Boehringer-Mannheim Biochemicals in accordance with the manufacturer's instructions. About 25 ng (⁻10 µCi label) of the probe were used per filter, and hybridization was conducted overnight at 37° C. in 50% formamide hybridization buffer. After hybridization, the filters were washed at room temperature six times; the first three washes were with 6×SSC containing 0.1% SDS, and the last three washes were with 6×SSC alone. After an initial exposure of several duplicate filters in a PhosphorImager™ cassette to check hybridization efficiency and signal strength, the filters were washed at 65° C. in 0.5×SSC. The filters were then placed under Kodak XAR5 film using two intensifier screens and allowed to expose the film for about 100 hours at −70° C.

One strong signal emanated from the filter containing a phage, later designated 28-1, comprising the gene for the RNA component of human telomerase. The plaque corresponding to the signal observed on the filter was used to make secondary plates, so that an isolated plaque (confirmed by probing with labeled pGRN7 nucleic acid) could be cultured for large-scale isolation of the phage DNA. Phage 28-1, available from the American Type Culture Collection under accession No. 75925, comprises an ⁻15 kb insert and comprises several restriction fragments that contain sequences that hybridize with RNA component sequences on pGRN7: a 4.2 kb EcoRI restriction enzyme fragment; a 4.2 kb ClaI restriction enzyme fragment, and a 2.5 kb HindIII-SacI restriction enzyme fragment. The latter fragment comprises the entire ⁻560 nucleotide sequence of the RNA component shown above and is believed to comprise the complete gene for the RNA component. The plasmid comprising the 2.5 kb HindIII-SacI restriction enzyme fragment in the pBluescript vector was designated plasmid pGRN33 and is available from the American Type Culture Collection under the accession No. ATCC 75926. Plasmid pGRN33 was deposited under the Budapest Treaty on Oct. 25, 1994 at the American Type Culture Collection, Rockville, Md. 20852. To the extent the human gene may comprise sequences other than those on the 2.5 kb fragment, those sequences can be isolated from phage 28-1 or from other phage clones identified by probing with the 2.5 kb fragment (or another probe of the invention). The restriction enzyme fragments noted above were prepared in separate restriction enzyme digests; the products of the digests were separated by electrophoresis on a 0.7% agarose gel or, for the ⁻2.5 kb fragment only, a 3% polyacrylamide gel; and the desired bands were cut from the gel and prepared for subcloning either by using the GeneClean™ Kit II (from Bio101, Inc.) or by electroelution into Spectropor #2 dialysis tubing in 0.1×TBE at 100 V for two hours (for the ⁻2.5 kb fragment only).

These restriction enzyme fragments were subcloned into E. coli expression/mutagenesis plasmids derived from pUC-based plasmids or from pBluescriptII plasmids that also comprise an SV40 origin of replication (but no SV40 promoter activity). The resulting plasmids can be used to prepare altered (mutated) RNA component nucleic acids for introduction into human or other eukaryotic cells for a variety of purposes, as described above in the Description of the Preferred Embodiments.

Example 8

Antisense Plasmids for the RNA Component of Human Telomerase

Antisense expression plasmids were prepared by PCR amplification of RNA component cDNA using the following primer sets: (1) NotB and G1, which produces an antisense nucleic acid that is smaller than the cDNA insert in the plasmid; and (2) NotB and R3C, which produces a full-length (relative to the insert in the plasmid) antisense nucleic acid. The nucleotide sequence of NotB is shown in Example 1, above; the nucleotide sequences of the G1 and R3C primers are shown below.

```
G1:   5'-GAGAAAAACAGCGCGCGGGGAGCAAAAGCA-3'

R3C:  5'-GTTTGCTCTAGAATGAACGGTGGAAG-3'
```

After PCR amplification, the amplified fragments were cloned into an ⁻10 kb expression plasmid at a PmlI site; the plasmid comprises puromycin resistance-conferring, DHFR, and hygromycin B resistance-conferring genes as selectable markers, the SV40 origin of replication; the inducible human metallothionein gene promoter positioned for expression of the antisense strand of the gene for the RNA component of human telomerase (one could also use a stronger promoter to get higher expression levels), and the SV40 late poly A addition site.

The resulting plasmids (designated pGRN42 for the NotB/G1 product and pGRN45 for the NotB/R3C product) were transfected by the calcium phosphate procedure (see Maniatis et al., supra) into the fibrosarcoma cell line HT1080. HT1080 cells are normally immortal; expression of the antisense RNA for the RNA component of human telomerase should prevent the RNA component of human telomerase from association with the protein components, blocking the formation of active telomerase and rendering the cells mortal.

Example 9

Identification and Isolation of RNA Component Nucleic Acids from Non-human Mammals To illustrate how the reagents of the invention can be used to identify and isolate substantially homologous nucleic acids from other mammalian species, PCR primers complementary to human RNA component sequences were used to amplify homologous sequences in a PCR. An illustrative primer pair used to demonstrate this aspect of the invention is composed of primer +10, which has the sequence 5'-CACCGGGT-TGCGGAGGGAGG-3' (SEQ ID NO:24), and primer R7, which has the sequence 5'-GGAGGGGCGAACGGGC- CAGCA-3' (SEQ ID NO:25). Genomic DNA was prepared from chimpanzee, squirrel monkey, rhesus monkey, and baboon tissue and dissolved in TE buffer at a concentration of about 0.5-4 mg/ml.

For each tissue type, a PCR mixture was prepared, which mixture comprised: 1 µL of genomic DNA, 48 µL of Master Mix (Master Mix is composed of 1×TaqExtender™ buffer from Stratagene, 200 µM of each dNTP, and 0.5 µM of each primer), and 0.5 µL of a 1:1 mixture of Taq polymerase (5 Units/µL, Boehringer Mannheim):Tth polymerase (TaqExtender™ polymerase, from Stratagene). The reaction tubes were loaded onto a thermal cycler, which was programmed to first heat the reaction mixture at 94° C. for 5 minutes and then to perform 27 cycles of incubations at 94° C. for 30 sec., 63° C. for 10 sec., and 72° C. for 45 sec. After the amplification reaction was complete, about 10 µL of each reaction mixture were loaded onto a 2% agarose gel for electrophoresis. After electrophoresis, staining of the gel, and UV irradiation, one could observe that each reaction mixture contained a band of the predicted (~200 bp) size. Nucleic acids from these bands can be cloned and sequenced and the remainder of the RNA component genes from each of these mammalian species can be cloned as described above for the gene for the RNA component of human telomerase.

Example 10

Mutated Sense hTR Sequences

This example demostrates that changing the hTR sequence at the template region alters the sequence synthesized by human telomerase, leading to changes in the chromosomal telomerase repeats.

To determine if re-programming the TRC3 template region would produce leads to corresponding changes in the telomere repeat synthesized in human telomerase activity, a gene fragment that expresses the entire hTR (TRC3) gene sequence was cloned and mutagenized. Southern blot analysis showed that TRC3 hybridized to a single-copy gene in the human genome. A genomic copy of TRC3 was isolated from a lambda phage library and shown to have the same restriction map as that observed on genomic Southern blots probed with TRC3. A 2.6 kb HindIII-Sac1 fragment was isolated and subcloned into a modified version of pBluescript, generating the genomic TRC3 plasmid pGRN33. The 5' and 3' ends of the RNA were mapped using primer extension, RACE PCR, and RT-PCR. The size of the RNA transcript was ≈550 bases, consistent with its migration on Northern blots. The transcribed region for TRC3 was central to the genomic clone with 1.4 kb of upstream sequence.

RNA was extracted from purified telomerase preparations and was then used in the following experiments. 5' RACE: First strand cDNA was made using antisense TRC3 primers (R3B: 5 '-CAACGAACGGCCA GCAGCTGACATT SEQ ID NO:27) in the presence of $^{32}$P-dATP. Extension products were resolved by PAGE and were identified by autoradiography, excised and extracted. An oligonucleotide (NotA: 5'-pATAGCGGCCGCTT GCCTTCA SEQ ID NO:28) was ligated to these first strand products using T4 RNA ligase and PCR was then performed using a nested primer, R3 c (5'-GTTTGCTCTAGAATGAACGGTGGAAG SEQ ID NO:23), and an oligonucleotide (NotB: 5'-TGAATTCT-TGCGGCCGCTAT SEQ ID NO:17) complementary to the NotA oligonucleotide. The PCR products were resolved on an agarose gel and bands were excised and sequenced directly, using oligonucleotide G1 (5'-AGAAAAA-CAGCGCGCGGGGAGCAAAGCA SEQ ID NO:29) as a primer. 3' end mapping: Attempts to perform 3' RACE were unsuccessful. Subsequently, an RT-PCR strategy was employed in which a series of antisense primers complementary to the genomic DNA sequence were used to prime first strand cDNA synthesis. The primers in this series were spaced at approximately 150 bp intervals starting from the 5' end of the transcript, proceeding towards the 3' end. PCR was then performed using the first strand primer and a primer whose sequence was internal to the known TRC3 transcript (F3b: 5'-TCTAACCCTAACTGAGAAGGGCGTAG SEQ ID NO:30). Reverse transcriptase-sensitive PCR bands of the predicted size were seen when using cDNA made with all primers designed to the interval +100 to +450 (numbering relative to 5' end) but not with any of the primers designed to +558 to +950. This placed the putative 3' end of the mature TRC3 transcript between position +450 and +558. Subsequent rounds of primer design and RT-PCR narrowed this interval to between +545 and +558.

The predicted template sequence of TRC3 was altered from CUAACCCUA; SEQ ID NO: 31 to C<u>C</u>AACCC<u>C</u>A; SEQ ID NO:32 (MuC) or C<u>A</u>AACCC<u>AA</u>; SEQ ID NO:9 (MuA) by in vitro mutagenesis (performed substantially according to Perez et al. (1994 *J. Biol. Chem*. 269: 22485) of the genomic plasmid pGRN33. If incorporated into functional telomerase, these mutant RNAs should template the synthesis of TTGGGG (MuC) or TTTGGG (MuA) rather than wild-type repeat TTAGGG.—These mutant telomerase activities could be easily distinguished from wild-type activity since they would no longer require dATP for activity and only the wild-type activity should be sensitive to termination by ddATP. A double mutant (MuC+17) was also prepared in which a 17 bp insertion was present at +180 bp in addition to the MuC template. This mutant allowed specific detection of the altered RNA with a probe to the 17 bp insertion or by size.

The 2.6 kb of genomic sequence was sufficient for expression of TRC3 in vivo. Cells were transiently transfected with the MuC+17 plasmid and RNA expressed from the transfected DNA was detected by RT PCR using the 17 bp insert sequence as the primer in the reverse transcription step. The RNA was detected in MuC+17-transfected cells but not in mock transfected cells, indicating that the 2.6 kb genomic clone was sufficient for TRC3 expression. Stable transformants were then derived from each of these three mutant plasmids by electroporation of HT1080 cells along with pCMVneo. Resistant clones were selected in G418 and expression of the MuC+17 RNA was verified by RT-PCR (Irving et al. (1992) *Exp. Cell Res*. 202: 161).

To test for mutant telomerase activity, the extracts were assayed from untransfected cells and from three stable transformants with integrated MuC*, MuC, or MuA vectors (C*, C, or A in FIG. 1). Since the mutant extracts were expected to contain both wild-type and mutant telomerase activities, various assay conditions were employed to distinguish between them. Under normal reaction conditions (dTTP, $^{32}$P-dGTP and dATP), all three extracts from the mutant construct series showed wild-type telomerase activity that was sensitive to RNase (FIG. 1, lanes 1-6). As expected, this activity was unaffected when ddCTP was included in the reactions (FIG. 1, lanes 7-9) and was abolished by ddTTP (lanes 10-12). In contrast, when ddATP was substituted for dATP, the C (lane 14) and A (lane 15) extracts still displayed RNase-sensitive (lanes 17 and 18) telomerase activity, while C* (lane 13) and control extract did not. These results indicate that the ddATP-resistant activities represent telomerase was reprogrammed with MuC or MuA TRC3 RNA. In contrast, the 17 bp insertion in C* inhibits reconstitution, indicating that telomerase reconstitution is very specific for the TRC3 sequence.

To confirm that the sequence synthesized by the mutant MuA was (GGGTTT)n, we modified the existing PCR methodology for amplifying telomerase repeats added onto a unique telomerase primer (Kim et al. (1994) *Science* 266: 2011). Using synthetic primers, we identified reaction conditions where a 3' primer with the sequence d(CCCAAAC-CCAAACCCAA) (SEQ ID NO:34) would only amplify (TTTGGG)n repeats and would not amplify (TTAGGG)n containing repeats.

To distinguish between telomeric repeats added by wild-type versus mutated telomerase, a two-step assay was combined with a strategy for limiting the availability of nucleotides for the telomerase reaction. Since MuA and MuC would generate telomeric repeat sequences of $(TTTGGG)_n$ and $(TTGGGG)_n$, respectively, cell extracts were first incubated with the TS substrate in the presence of only dTTP and dGTP for 10 min at room temperature to allow for the addition of telomeric repeats. Residual telomerase activity was then destroyed by boiling the extracts for 5 min. Telomerase products with specific DNA sequence were then detected by PCR amplification using the appropriate reverse primers and in the presence of all 4 dNTP's and trace amounts of $^{32}$P-dCTP as described (Kim et al. (1994) op.cit). To detect the MuA products, the reverse primer was $(ACCCAA)_4$ (SEQ ID NO:34) and the PCR conditions were 94° C., 10 sec, 60° C., 30 sec and 72° C., 30 sec for 20 cycles. To detect the MuC products, three reverse primers were used: $(CCCCAA)_3$ (SEQ ID NO:35), $(CCAACC)_3$ (SEQ ID NO:36) and $(CCAACC)_3$ (SEQ ID NO:36), respectively, which gave PCR products with the corresponding mobility shifts consistent with the expected position of annealing to the telomerase products. The PCR conditions used were the same as above, except that the annealing temperature was 50° C. Under the same conditions, no telomerase products were generated from extracts of parental cells or cells transfected with the wild-type TRC-3 gene. In tests of the specificity of our PCR amplification conditions, synthetic oligbnucleotides containing $(TTTGGG)_n$ and $(TTGGGG)_n$ generated the appropriate 6 nt ladder PCR products with $(ACCCAA)_4$ (SEQ ID NO:34) or $(CCCCAA)_3$ (SEQ ID NO:35) reverse primer respectively, whereas $(TTAGGG)_n$ oligonucleotides did not produce any PCR products with the $(ACCCAA)_4$ (SEQ ID NO:34) or $(CCCCAA)_3$ (SEQ ID NO:35) reverse primer Using these conditions, extracts from MuA but not from MuC or wild type cells generated products in the modified telomerase assay, indicating that telomerase from MuA containing cells generated (TTTGGG)n repeats. Similar methods were used to analyze the MuC mutant, which synthesized (TTGGGG)n repeats. Together, the above data constitute strong evidence that the TRC3 gene encodes the RNA component of human telomerase, and thus we have renamed TRC3 as hTR for <u>h</u>uman <u>T</u>elomerase <u>R</u>NA.

Example 11

Expression of hTR in Mortal and Immortal Cells

Figure 2A:
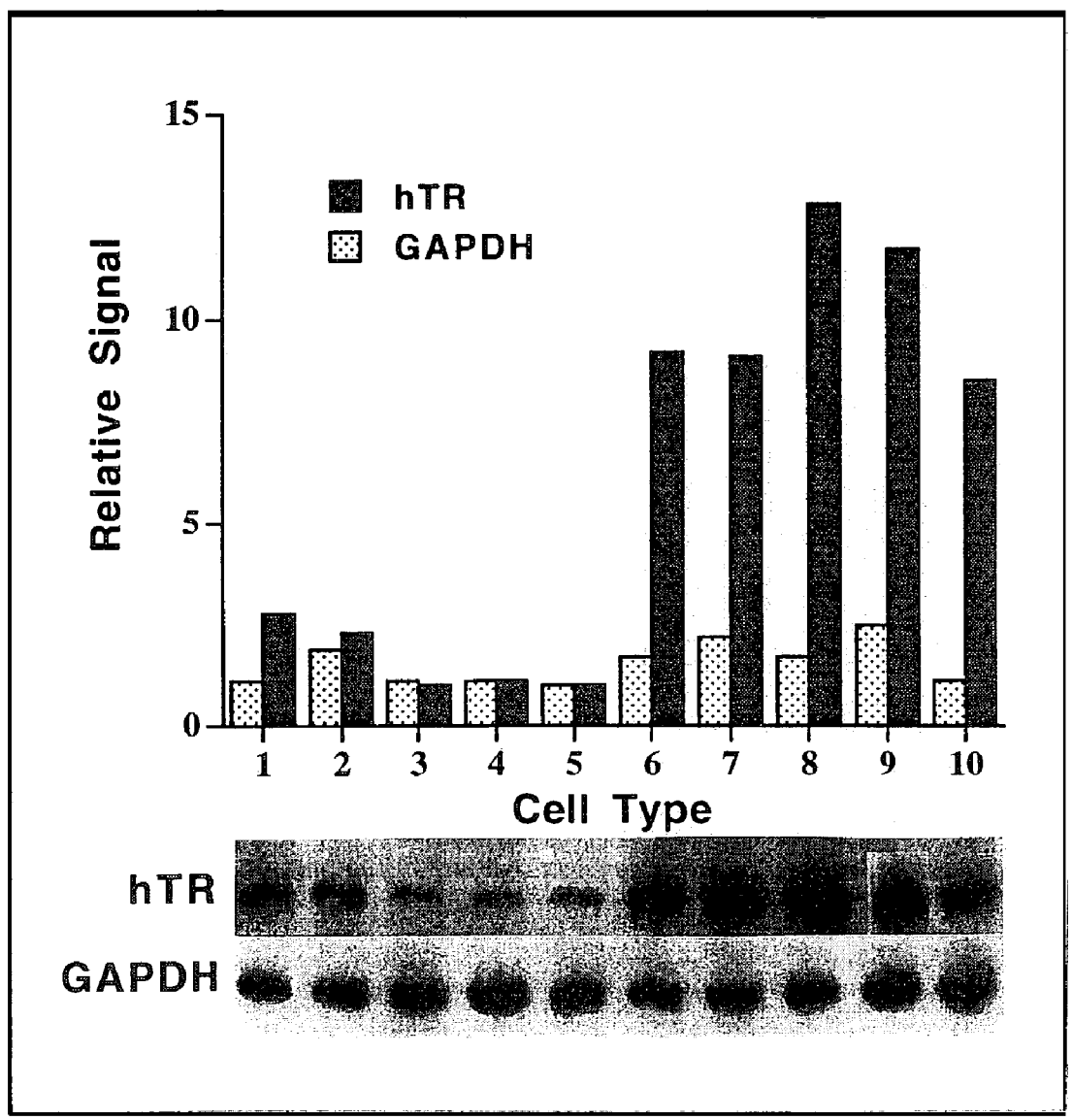
FIG. 2A. The steady-state level of hTR and GAPDH RNA was determined using quantitative RT-PCR. Controls show that all PCR quantitations were in the linear range up to 25 cycles. RT-PCR was analyzed for five normal telomerase-negative cell lines (1-5) and five tumor telomerase-positive cells lines (6-10): 1) Primary fetal lung; 2) Primary fetal hand skin; 3) Adult primary prostate; 4) Primary sinovial fibroblasts; 5) Foreskin fibroblasts; 6) Melanoma LOX; 7) Leukemia U25x; 8) NCIH23 lung carcinoma; 9) Colon tumor SW620; 10) Breast tumor MCF7. PCR products were labeled with $^{32}$P, resolved on a 6% PAGE, and quantified using a PhosphorImager. The relative transcription is expressed in arbitrary units.

Most cancer cells express high levels of telomerase activity, while in most normal somatic human cells, telomerase is not detected (Kim et al. (1994) op.cit). To determine if hTR RNA levels are elevated in immortal cancer cell lines, hTR and GAPDH transcript levels were analyzed using RT-PCR in five mortal primary cell strains, which lacked detectable telomerase activity, and five immortal cancer cell lines with high levels of telomerase activity. The steady state levels of hTR transcripts was 3- to 12-fold higher in the tumor cell lines than in primary cells when compared to the levels of GAPDH (FIG. 2A). While hTR levels were increased in the immortal cancer cells expressing high levels of telomerase, it is interesting that low but readily detectable levels of hTR RNA were also present in mortal primary cells with no detectable telomerase activity (lanes 1-5).

Figure 2B:
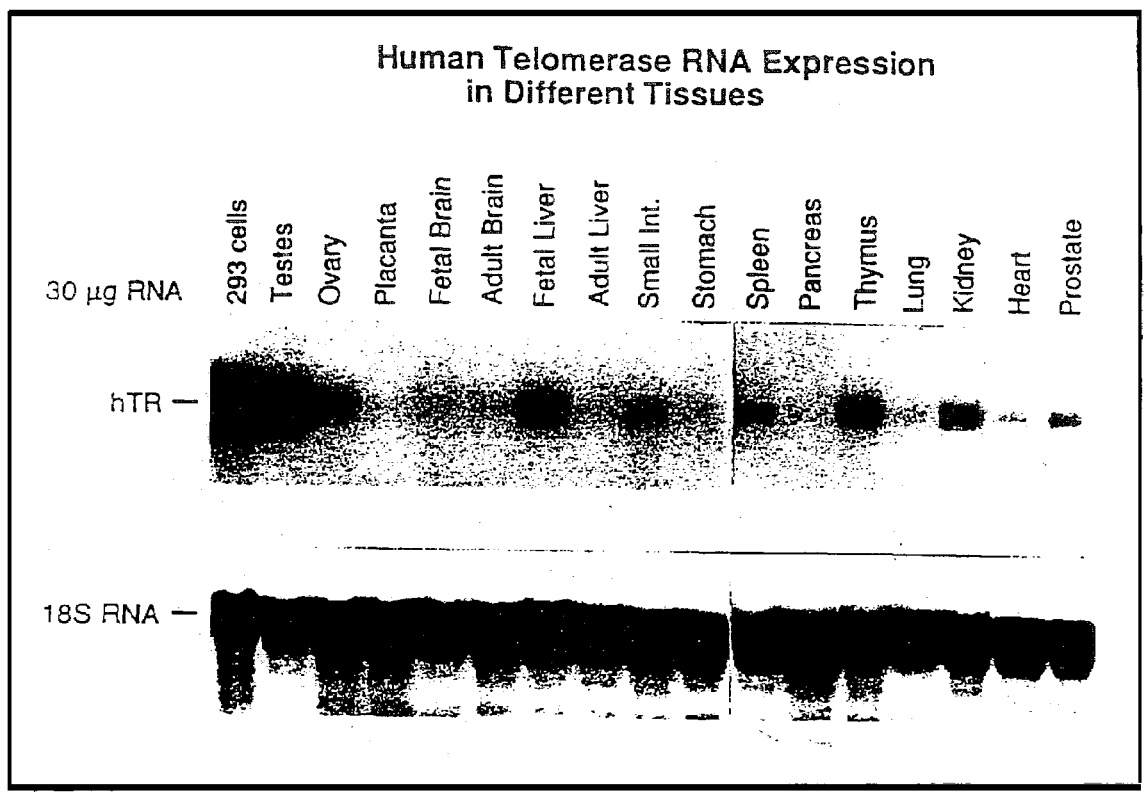
FIG. 2B. Northern blot of hTR RNA prepared from human tissues. Total 293 RNA was prepared by guanidinium thiocyanate-phenol/chloroform extraction and tissue RNAs were obtained from Clonetech. Thirty micrograms of total RNA was loaded onto a 1.5% agarose/formaldehyde gel and transferred onto Hybond N. The blot was probed with the human telomerase RNA in Church hybridization solution. Telomerase RNA was detected in all tissues, with the highest level of expression seen in the testes and ovary. As a control for loading, the blot was washed and re-probed for 18S rRNA.
Figure 2C:
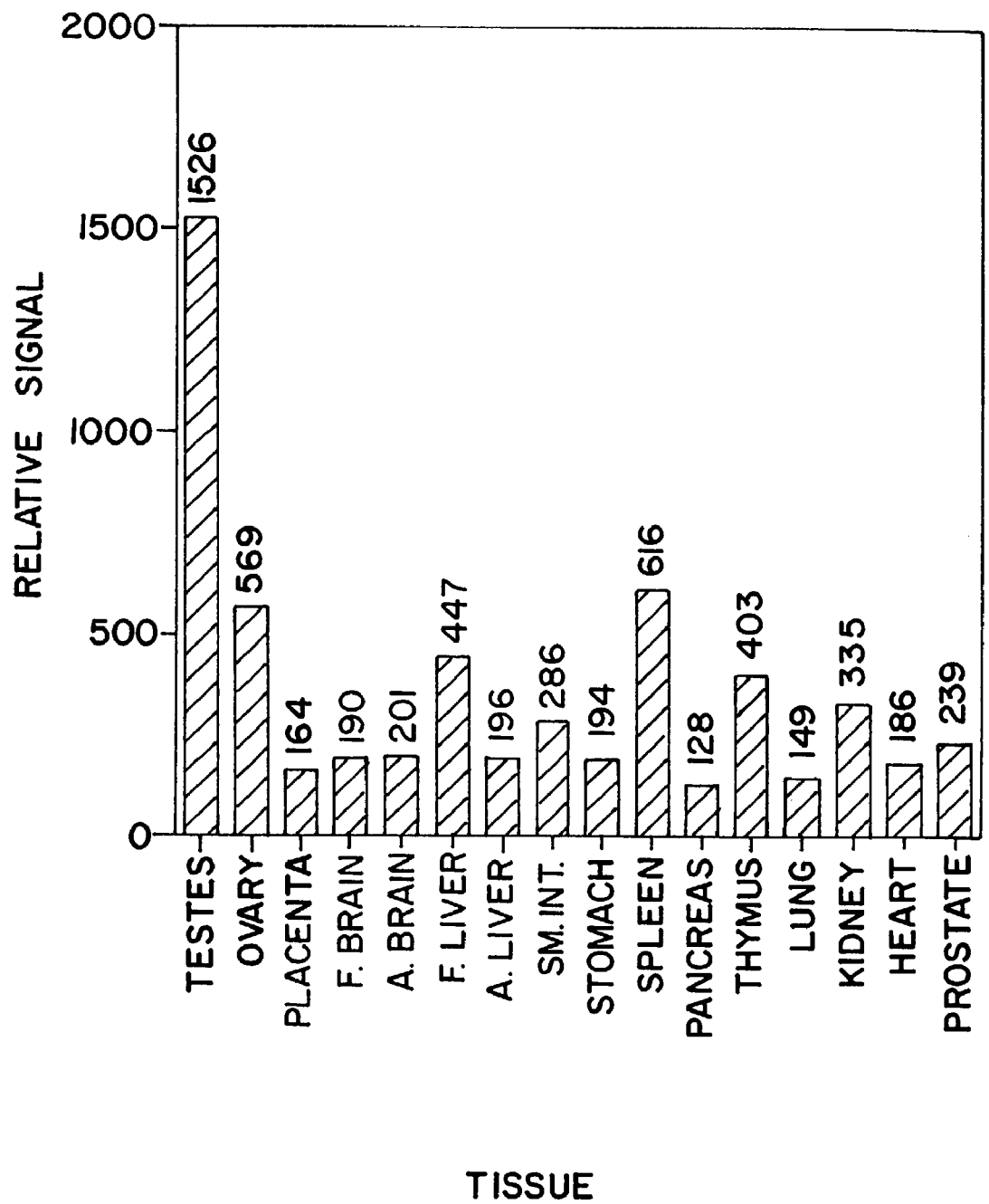
FIG. 2C. Histogram of the relative levels of telomerase RNA in different tissues. The Northern hybridization signals were quantified on a PhosphorImager and the hTR was normalized to the 18S loading control. The relative signal is expressed as arbitrary units.

The hTR levels were also examined in a variety of normal human tissues by Northern blot analysis. Testes and ovary had the highest level of hTR, which was expected since these tissues express high levels of telomerase activity. However, a number of other tissues also expressed hTR (FIGS. 2B and 2C). These include normal kidney, prostate, and adult liver, all of which lack detectable levels of telomerase activity. These results confirm the data from cell lines (FIG. 2A) and suggest that telomerase RNA may be present but inactive in a number of human tissues. Similar tissue-specific differences in RNA expression are seen in mouse tissues; however, many normal mouse tissues are positive for telomerase activity. The apparent increased repression of telomerase activity in human cells may help explain why mouse cells spontaneously immortalize in culture while human cells do not.

Example 12

Expression of Antisense hTR (Human Telomerase RNA Component) Transcripts in HeLa Cells Leads to Cell Crisis and Cell Death To examine the function of telomerase in an immortalized cell, antisense hTR expression constructs were introduced into HeLa cells. A 200 bp EcoRI DNA fragment containing 1 to 193 bp of a human telomerase RNA component cDNA clone, TRC3, was inserted into the EcoRI site of p10-3 and pBBS212 to generate plasmids p10-3-hTR and pBBBhTR, respectively. Plasmid p10-3-hTR expresses the antisense of hTR under the transcriptional control of the tetracycline-regulated CMV minimal promoter relative to the five Tet-operators upstream in two different orientations as described (Gossen et al. (1992) *Proc. Natl. Acad. Sci.* (*USA*) 89: 5547). Plasmid pBBS-hTR expresses the antisense of hTR under the control of the MPSV promoter (Lin et al. (1994) *Gene* 147: 287). In parallel, control expression vectors lacking the antisense hTR coding sequence were also electroporated into HeLa cells. Clones containing antisense or control plasmids were selected in three separate experiments. Initially, the 41 cultures expressing antisense hTR grew identically to cells with the control vector. However, at 23 to 26 population doubling levels (PDL) post-transfection, 33 out of 41 antisense expressing cultures underwent crisis (Table I). Cell crisis in these cultures was characterized by a marked inhibition in cell growth from 20 to 26 PD, followed by the rounding up and detachment of cells from the plate over a period of a week. In 28 out of 33 cases in which the cells underwent crisis, rare (<1%) revertant colonies were observed within three weeks after most of the cells had died. The revertant cells may represent variants that escape the inhibiting effect of the antisense hTR construct. In contrast to the antisense clones, none of the vector control cell lines had any change in growth or mortality over 50 doublings.

TABLE I

Antisense hTR leads to shorter mean TRF and cell crisis
Three independent experiments were carried out in which HeTe7 cells (HeLa cells that express high levels of the tetracycline repressor-VP16 chimeric protein) were transfected by electroporation with either plasmid p10-3-hTR, expressing antisense hTR under control of the tetracycline-VP16-induced CMV minimal promoter or pBBS-hTR, expressing antisense hTR under the control of the MPSV promoter (54). [In these experiments no regulation by tetracycline was observed. The experiments with p10-3-hTR were typically carried out in the absence of tetracycline, because control experiments with luciferase or antisense hTR under the control of the tetracycline-VP16-induced CMV minimal promoter demonstrated that the presence or absence of tetracycline had little effect on luciferase or antisense hTR expression in HeTe7 cells. Indeed, in early experiments with antisense hTR constructs in HeTe7 cells, the cells still underwent crisis at 23 to 26 PDL in the presence of tetracycline.]. As a control, HeTe7 cells were also transfected with the parental vector under the same conditions. Eleven to eighteen stable clones were isolated from each transfection series. Clones from all isolates displayed identical morphology and growth profiles until 20 PDL, at which time the growth of most of the antisense-expressing clones slowed markedly (p10-3-hTR and pBBS-hTR). By PDL 23–26, these cells underwent crisis, characterized by the appearance of enlarged and rounded cells. However, not all of the clones generated from the pBBS-hTR transfected HeTe7 cells underwent crisis; eight clones expressing antisense hTR continued growing similar to the control cultures. Cells from all clones were harvested at PDL 23 and the mean TRF lengths were determined. The P values were calculated by the method of unpaired t-test. For each series, the proportion of clones that underwent crisis is indicated.

|   | Plasmid | Cell Crisis | Mean TRF | P Value | Crisis/Total |
|---|---------|-------------|----------|---------|--------------|
| 1 | p10-3 | no | ND |  | 0/7 |
|   | p10-3-hTR | yes | ND |  | 18/18 |
| 2 | p10-3 | no | 3.27 ± 0.10 | 0.0003 | 0/12 |
|   | p10-3-hTR | yes | 2.72 ± 0.07 |  | 11/11 |
| 3 | pBBS | no | 3.22 ± 0.11 | 0.0008 | 0/13 |
|   | pBBS-hTRa | yes | 2.39 ± 0.10 |  | 4/4 |
|   | pBBS-hTRb | no | 3.03 ± 0.20 | 0.3551 | 0/8 |
|   | HeTe7 cells | no | 3.15 ± 0.09 |  | Parental cells |

Figure 3:
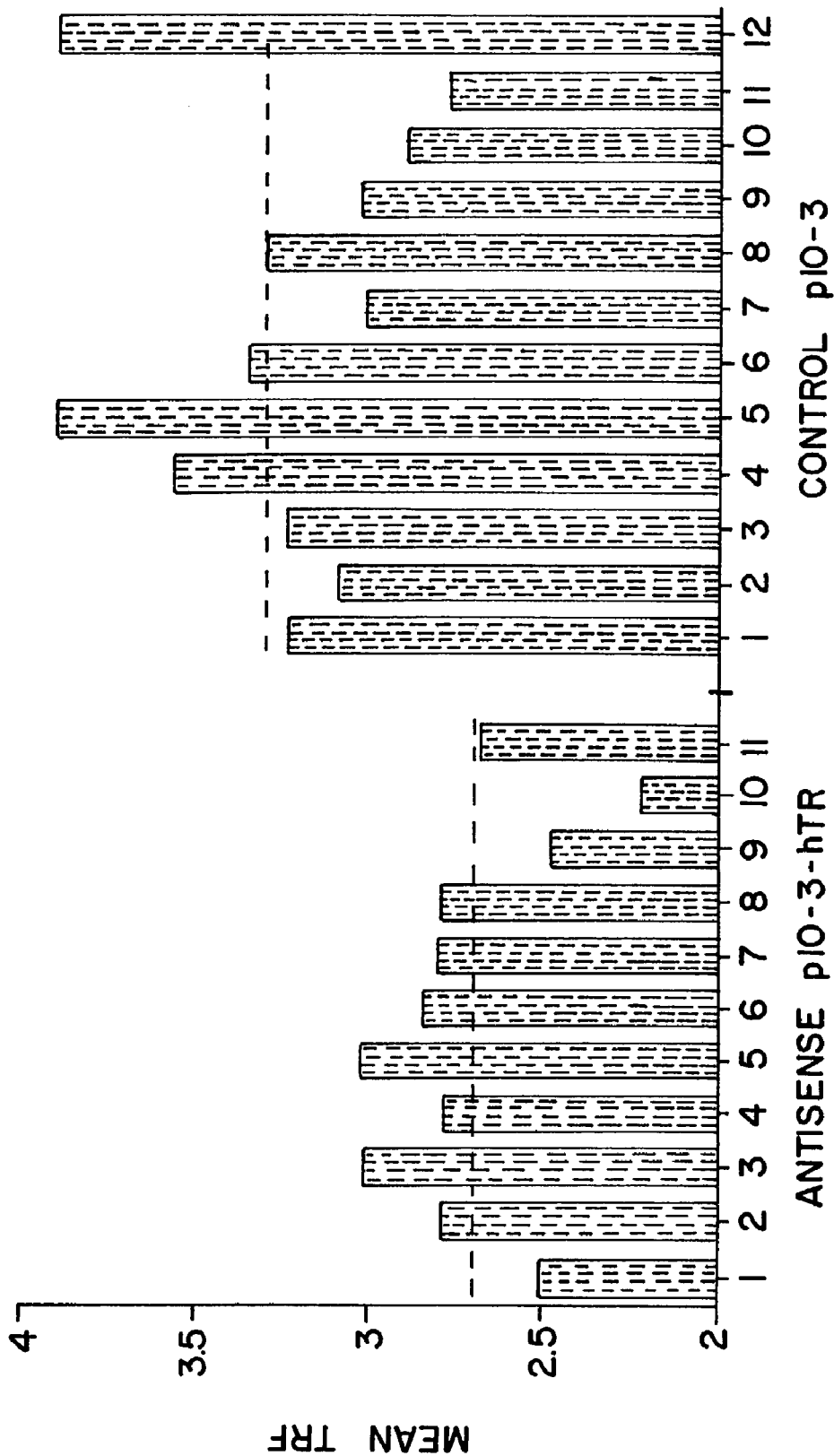
FIG. 3. Mean TRF length in hTR antisense and vector control cells. HeTe7 cells that stably express 10-3-hTR antisense or vector control were selected in hygromycin and puromycin media and harvested at 23 PDL post transfection. Nuclear DNA was purified, cut with HinfI and RsaI, and run on a 0.5% agarose gel. The DNA was probed in the gel with a (TTAGGG)$_3$ SEQ ID NO:26 oligonucleotide to label the telomeric terminal restriction fragments (TRF). The gel was scanned with a Molecular Dynamic's PhosphorImager and the mean TRF quantitated as described (Allsopp et al. (1992) *Proc. Natl. Acad. Sci. (USA)* 89: 10114). The dashed lines indicate the average mean TRF for the antisense and control groups.

To determine if telomere length and telomerase inhibition correlated with cell crisis in the antisense expressing clones, telomere length and telomerase activity in several precrisis control and experimental colonies were assayed at 23 PDL. All colonies containing control vector had mean TRF lengths (3.22 and 3.27 kb) similar to the parent cell line (3.15 kb), whereas clones containing the antisense vector constructs that underwent crisis had mean TRF lengths between 2.39 and 2.72 kb or 17 to 26% shorter than those of the parental line (FIG. 3). These data are consistent with telomere repeats being lost in the antisense containing clones due to the inhibition of telomerase activity. To test this directly, telomerase activity was assayed in 14 of the clones. Telomerase activity was generally low but detectable in many of the antisense clones, although the shortened telomeres suggest that the level was not sufficient to maintain telomere length since mean TRF fell from 3.22 to 2.39 kb (P=0.0008). In the eight clones containing the antisense vector (pBBS-hTRb) that did not undergo crisis, telomere length was not significantly changed (3.03 versus 3.33, P=0.355), and telomerase activity was similar to that of controls. Taken together, these results are evidence that telomere loss leads to crisis and cell death once telomeres reach a critical length.

The induction of cell crisis in HeLa cells expressing antisense hTR provide further support that telomerase inhibition can provide a specific and effective therapeutic against human cancer.

Example 13

In situ Amplification and Detection

In Situ Detection of Telomerase RNA

A. Fluorescent in situ Hybridization (FISH)

Identification of telomerase positive cells in a mixed population of cells or tissues can be peformed by in situ hybridization of labeled probe targeted at the RNA component of telomerase. A tissue of cell samples fixed onto a microscopic glass slide and permeabilized sufficiently ζ used for in situ hybridization. An example of in situ hybridization for human telomerase RNA (htRNA) consist of first denaturing the nucleic acids by immersing the slides in 70% deionized formamide/2×SSC solution pre-warmed to 70-74° C. for 2-3 min. The slides are then transferred to ice-cold 70% EtOH, and then to 95% EtOH, and then to 100% EtOH (4 min. in each solutions). 100-200 ng (per slide) of the labeled htRNA probe (~500 bp DNA probe labeled with biotin, digoxigenin, radioisotope, fluorescent tag) is dried, resuspended in 10 µl of 100% deionized formamide, denatured by incubation at 75° C. for 8 min., and immediately cooled on ice. Add 10 µl of 2×hybridization buffer (4×SSC; 4×Denhardt's solution; 20% dextran sulfate; 100 mM Tris, pH 7.5) to the 10 µl of resuspended probe. Add the probe/hybridization mix (20 µl) to the fixed sample, overlay with a coverslip, and seal the coverslip with rubber cement or nail polish. Incubate the sample at 37° C. for 8-48 hr. After the hybridization, remove the coverslip, wash the sample twice in 2×SSC/50% deionized formamide at 37° C., and then wash twice in 2×SSC at 37° C. (5 min. per wash). The sample is then viewed under a microscope.

B. Primed-in situ Labeling (PRINS)

Another variation to the traditional in situ hybridization detection method is Primed-in situ labeling (PRINS) Detection of the htRNA by PRINS consist of initial cDNA synthesis of the htRNA by reverse transcriptase (RT) followed by PRINS detection using htRNA-specific oligonucleotide probe and chain elongation incorporating labeled nucleotides. RT reaction of the htRNA can be performed by variety of methods. One example of the RT reaction is by using GeneAmp Thermostable rTth Reverse Transcriptase RNA PCR kit (Perkin Elmer). In this method, 10 µl of RT mix (10 mM Tris-HCl pH 8.3; 90 mM KCl; 1 mM MnCl$_2$; 200 µM dNTPs; 2.5 U rTth DNA polymerase; 0.4 µM return primer [e.g., R7G: 5'-GGAGGGGCGAACGGGCCAGCAG-3']) is placed on the fixed and permeabilized sample (Sec. I.B), sealed with coverslip, anchored with nail polish, overlayed with mineral, and incubated at 70° C. for 30 min. Afterwards, the mineral oil is removed by washing for 5 min in xylene, and then 5 min in 100% EtOH. The coverslip is taken off, washed briefly with DepC water, then with 100% EtOH, and air dried for 5 min. Then 10 µl of PRINS mixture (5% (v/v) glycerol; 10 mM Tris-HCl, pH 0.3; 100 mM KCl; 0.05% (w/v) Tween 20; 0.75 mM EGTA; 2.5 mM MgCl$_2$; 0.4 µM forward prime [e.g. U3b: 5'-GCCTGGGAGGGGTGGTGGC-TATTTTTTG-3']; 200 µM dA, dG, dCTP; 110 µM dTTP; 90 µM labeled dUTP) is placed on the sample. Sealed with coverslip, anchored with nail polish, overlayed with mineral oil, and incubated at 70° C. for 30 min to 3 hr. As soon as the last PCR step is completed, the sample is washed 3 times in the wash buffer (4×SSC; 0.05% Tween 20) heated to 70° C., for 2 min. The signal is then observed.

C. In situ RT-PCR

RT-PCR detection of htRNA consist of cDNA synthesis of the target RNA by reverse transcriptase reaction (viral reverse transcriptase, or by the intrinsic RT activity of thermostable DNA polymerases), followed by in situ PCR amplification of the target cDNA. Various RT reactions can be used in the cDNA synthesis of the htRNA including the RT protocol discussed in Sec. II.B. Furthermore, the same buffer condition and the primers used in the PRINS detection methods can also be used for RT-PCR, only difference being that instead of final incubation at 70° C. for 30 min to 3 hr, the sample would be amplified in a thermocycler for 30-40 cycles of 94° C./40 sec, 55° C./90 sec (see Sec. II.B.). As soon as the last PCR step is completed, the sample is washed 3 times in the wash buffer (4×SSC; 0.05% Tween 20) heated to 70° C., for 2 min. The signal is then observed.

Another alternative is to amplify the cDNA generated from the initial RT reaction by using the GeneAmp in situ PCR system 1000 and GeneAmp in situ PCR core kit (Perkin Elmer).

One step in situ RT-PCR on a fixed and permeabilized sample can be performed using GeneAmp EZ rTth RNA PCR protocol in combination with GeneAmp in situ PCR system 1000 (Perkin Elmer). This method consist of placing 40-50 µl of EZ RNA PCR buffer mix (50 mM Bicine; 115 mM potassium acetate; 8% (w/v) glycerol, pH 8.2; 300 µM dA, dG, dCTP; 165 µM dTTP; 135 µM labeled dUTP; 5-10 U of rTth DNA polymerase; 2.5 mM Mn(OAc)$_2$; 0.45-1 µM of htRNA-specific primers e.g. R7 and U3b. onto a fixed and permeabilized sample on a microscopic slide, and sealing it with the silicone gastket and clip following the manufacturer's protocol (GeneAmp in situ PCR system 1000, Perkin Elmer). The sample is then placed in GeneAmp in situ PCR machine and heated for 120 sec at 94° C., and then amplified for 30-40 cycles of 94° C./45 sec, and 60° C./45 sec. After the amplification, the sample is washed and visualized as discussed previously.

To reduce the background signals that can arise from direct incorporation of fluorescent tags during the PCR amplication, indirect detection that consist of PCR amplification using non-tagged dNTPs followed by in situ hybridization utilizing a tagged hybridization probe specific for the amplified product can be used. In this method, the signal is amplified by any of the RT-PCR method described above without labeled dNTPs or primers, and the amplified product is detected by in situ hybridization.

D. Application of Product Extension Primer to in situ PCR

The success of in situ PCR depends on the prevention of the amplified products inside the cellular matrix from leaking out of the cell. Therefore, it is generally true that the PCR product smaller than 500 bp is not desirable for in situ PCR. In order to prevent the leakage of the PCR products smaller than 500 bp from the cellular matrix, incorporation of "bulky" dNTPs (e.g., biotin, fluorescent tag, digoxigenin labeled dUTP) into the PCR product is commonly used. Another way to prevent the leakage of a small products in in situ PCR would be to incorporate product extension primer into the in situ PCR protocol.

Figure 4:
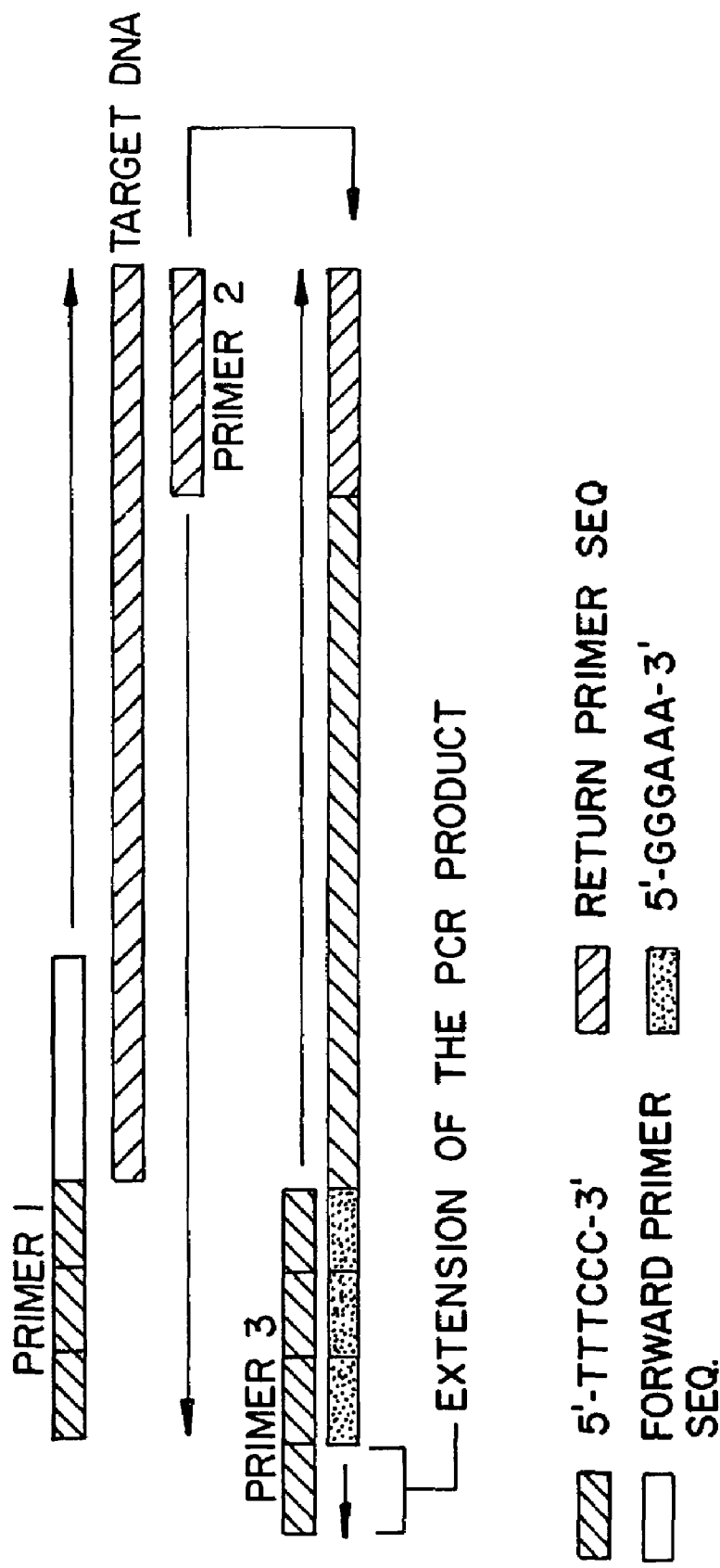
FIG. 4 Schematic representation of in situ PCR method.

The method consists of using a primer that contains 3-4 6 bp repetitive sequence (e.g. [5'-TTTCCC-3']$_{3-4}$ SEQ ID NO:37 and 38) at the 5' end, followed by a sequence that is specific for the target (see FIG. 4, primer 1), in combination with appropriate return primer (primer 2), and a third primer that consist solely of the repetitive sequence (primer 3, e.g. [5'-TTTCCC-3']$_4$ SEQ ID NO:38) to amplify the specific target in in situ PCR. The presence of the primer 3 will elongate the PCR product due to the staggered-binding of the primer 3 to 3'-end of the target PCR product. The elongation of the PCR products can be induced by decreasing the annealing temperature of the initial PCR condition.

For example, if the annealing temperature of the target sequence in the primer 1 is 60° C., the sample will be initially amplified for 15-20 cycles of 94° C./45° C. and 60° C./45° C., then it will be amplified for 15-20 cycles of 94° C./45° C. and 50° C./45° C. Lowered annealing temperature in the second PCR step will favor the generation of the elongated PCR products by increasing the chance of stagger-binding of primer 3 to the repetative sequences. The resulting elongated PCR products will be less prone to leakage through the cellular matrix, thus resulting in a better signal retention in in situ PCR analysis.

The foregoing examples describe various aspects of the invention and how certain nucleic acids of the invention were made. The examples are not intended to provide an exhaustive description of the many different embodiments of the invention encompassed by the following claims.

The invention claimed is:

1. A method for inhibiting telomerase activity in human cells in vitro, the method comprising the step of contacting the cells in vitro with a polynucleotide comprising a ribozyme in an amount sufficient to inhibit telomerase activity, the ribozyme comprising a nucleotide sequence of 5'UAGGG-UUACUGAUGAGUCCGUGAGGACGAAA-CAAAAAAU-3' (SEQ ID NO:12) wherein the ribozyme inhibits endogenous telomerase activity in the cell in vitro.

2. The method of claim 1, wherein the cells are cancer cells.

3. The method of claim 1, wherein the step of contacting the cells in vitro comprises transfecting the cells with an expression vector comprising a heterologous transcription regulatory sequence operably linked to a polynucleotide sequence that encodes the ribozyme, wherein the transcription regulatory sequence promotes transcription of the ribozyme in the cell.

4. The method of claim 3, wherein the heterologous transcriptional regulatory sequence comprises a promoter which is constitutively active in human cells.

5. The method of claim 3, wherein the expression vector is an adenovirus-based vector.

6. The method of claim 3, wherein the heterologous transcriptional regulatory sequence is selected from metallothionein promoter, constitutive adenovirus major late promoter, dexamethasone-inducible MMTV promoter, SV40 promoter, MRP polIII promoter, constitutive MPSV promoter, tetracycline-inducible CMV promoter, and constitutive CMV promoter.

7. The method of claim 1, wherein the ribozyme is a hammer head ribozyme or a Group I intron ribozyme.

* * * * *